United States Patent [19]

Whittle et al.

[11] Patent Number: 4,762,835
[45] Date of Patent: Aug. 9, 1988

[54] PYRIMIDINE DERIVATIVES

[75] Inventors: Alan J. Whittle, Aldershot; Roger Salmon, Bracknell; Edward McDonald, Marlow, all of England

[73] Assignee: Imperial Chemical Industries PLC, London, England

[21] Appl. No.: 942,436

[22] Filed: Dec. 16, 1986

[30] Foreign Application Priority Data

Dec. 23, 1985 [GB] United Kingdom ............... 8531637

[51] Int. Cl.$^4$ ................. A61K 31/505; C07D 239/02; C07D 401/02; C07F 7/02
[52] U.S. Cl. ..................................... 514/256; 544/229; 544/333; 544/334; 544/335
[58] Field of Search ............... 544/333, 334, 335, 229; 514/256

[56] References Cited

U.S. PATENT DOCUMENTS 4,661,488  4/1987  McDonald et al. ................ 544/335

Primary Examiner—Mary Lee
Assistant Examiner—Zinna Northington

Attorney, Agent, or Firm—Cushman, Darby & Cushman

[57] ABSTRACT

A compound of formula:

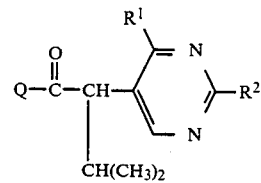

wherein $R^1$ represents hydrogen or halogen, $R^2$ represents an α-branched alkyl or a cycloalkyl group containing from 3 to 6 carbon atoms, Q represents hydroxy, halo, alkoxy of up to 6 carbon atoms or a group —OR where R represents the residue of an alcohol of formula ROH which forms an insecticidal ester when combined with crysanthemic acid, or 3-(2,2-dichlorovinyl)-2,2-dimethylcyclopropane carboxylic acid, or 3-(2-chloro-3,3,3-trifluoroprop-1-en-1-yl)-2,2-dimethylcyclopropane carboxylic acid. The compounds are useful for combating insect and acarime pests.

7 Claims, No Drawings

PYRIMIDINE DERIVATIVES

This invention relates to novel acids and derivatives thereof useful as intermediates, and to insecticidally active esters of these acids and compositions comprising them. The invention also relates to processes for preparing the novel acids and derivatives and to novel compounds useful in such processes.

In a first aspect this invention provides novel compounds of formula I:

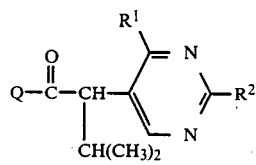

wherein $R^1$ represents hydrogen or halo, $R^2$ represents an α-branched alkyl group or a cycloalkyl group containing from 3 to 6 carbon atoms, and either (a) Q represents hydroxy, halo (especially chloro) or alkoxy of up to 6 carbon atoms, wherein such compounds are useful as intermediates for insecticides, or (b) Q represents the group —OR where R is the residue of an alcohol of formula ROH which forms an insecticidal ester when combined with chrysanthemic acid or permethrin acid or cyhalothrin acid. Permethrin acid is 3-(2,2-dichlorovinyl)-2,2-dimethylcyclopropane carboxylic acid and cyhalothrin acid is 3-(2-chloro-3,3,3-trifluoroprop-1-en-1-yl)-2,2-dimethylcyclopropane carboxylic acid.

More particularly Q represents a group of the following general formula:

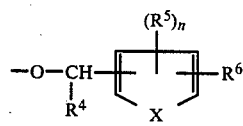

wherein X is oxygen, sulphur, vinylene or a group of formula $-CR^5=Y-$ where Y is nitrogen or $CR^5$, $R^4$ is hydrogen, methyl, cyano or ethynyl, each $R^5$ is selected from hydrogen, halogen, alkoxy of up to four carbon atoms and alkyl of up to 4 carbon atoms optionally substituted with halogen, n is selected from 0, 1 or 2 and $R^6$ is hydrogen, halogen, alkyl of up to 4 carbon atoms, alkoxy of up to four carbon atoms, alkenyl of up to 6 carbon atoms, haloalkenyl of up to 6 carbon atoms, alkynyl of up to 4 carbon atoms, alkoxyalkyl of up to a total of 4 carbon atoms, phenyl, phenoxy or benzyl, or phenyl, phenoxy or benzyl substituted with halogen or alkyl.

It will be appreciated that the compounds of formula I are capable of existing in different isomeric forms and as mixtures of isomers. Thus optical isomerism arises from the presence of one or two chiral centres leading to the possibility of stereoisomers or diastereoisomers. In addition the possibility of geometrical isomerism arises where the alcohol moiety contains a substituted alkenyl group. All such individual isomeric forms and mixtures thereof, including racemates, are within the scope of the invention.

Specific compounds according to formula I useful as intermediates are those wherein Q represents an alkoxy group of up to 6 carbon atoms, including the methyl, ethyl, propyl and butyl esters of the acids of formula I wherein $R^1$ is hydrogen, chloro or fluoro, and $R^2$ is one of prop-2-yl, but-2-yl, pent-2-yl, pent-3-yl, 2-methylprop-2-yl, 2-methylbut-2-yl, cyclopropyl, 1-methylcyclopropyl, and cyclohexyl.

Particular compounds useful as intermediates include the following:

ethyl RS-2-[2-(prop-2-yl)pyrimidin-5-yl]-3-methylbutyrate, ethyl RS-2-[2-(1-methylcycloprop-1-yl)pyrimidin-5-yl]-3-methylbutyrate, ethyl RS-2-(2-prop-2-yl)pyrimidin-5-yl)-3-methylbutyrate, ethyl RS-2-[2-(2-methylbut-2-yl)pyrimidin-5-yl]-3-methylbutyrate, ethyl RS-2-(2-cyclopropylpyrimidin-5-yl)-3-methylbutyrate, ethyl RS-2-[4-chloro-2-(2-methylprop-2-yl)pyrimidin-5-yl]-3-methylbutyrate, ethyl RS-2-[4-fluoro-2-(2-methylprop-2-yl)pyrimidin-5-yl]-3-methylbutyrate, together with each of the corresponding carboxylic acids, and the acid chlorides derived therefrom.

The compounds of formula I wherein $R^1$ is hydrogen or halogen, $R^2$ is as defined above and Q represents a group—OR where —OR is alkoxy of up to 6 carbon atoms may be prepared by alkylation of the corresponding compound of formula:

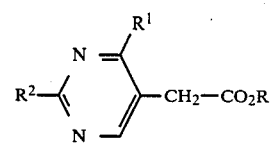

with a 2-halopropane in the presence of a base. 2-Iodopropane is particularly useful in the process and a suitable base is lithium hexamethyldisilylamide (LHMDS). The compounds of formula A may be prepared, for example, by the reaction of the appropriate amidine with a dialkyl ester of 1-formylsuccinic acid, followed by conversion of the 4-hydroxy to the 4-halo or 4-hydrogen compound of formula A.

By way of exemplification this process is set out below as a scheme for the preparation of the compounds of formula I wherein $R^1$ is hydrogen or halogen, $R^2$ has any of the meanings described hereinbefore, and Q represents —OR, wherein —OR is alkoxy of up to 6 carbon atoms.

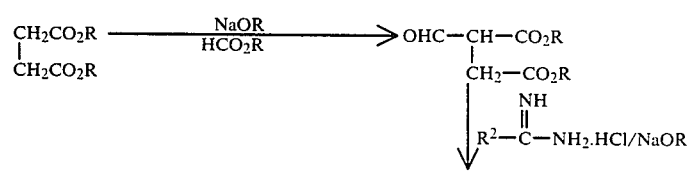

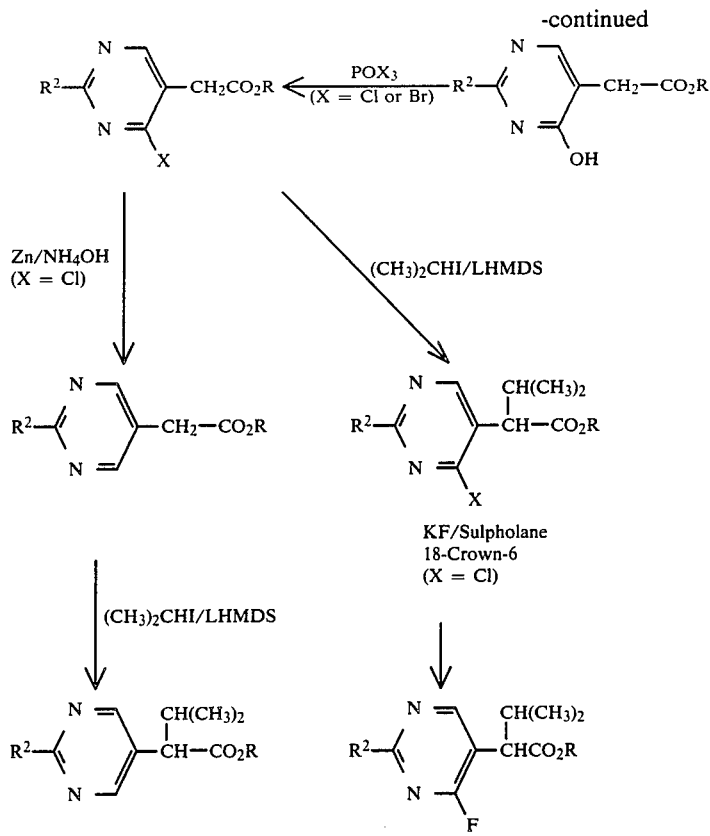

In the particular case where $R^1$ is hydrogen these alkoxy esters may alternatively be prepared according to the following scheme.

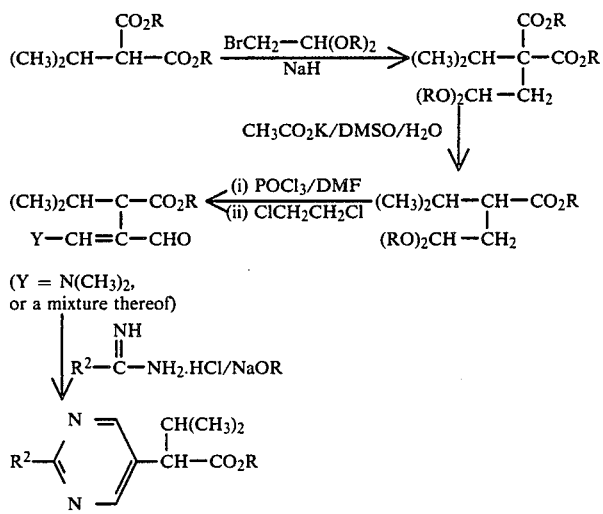

The compounds of formula I wherein Q represents hydroxy may be obtained by hydrolysis of the alkyl esters described above, preferably by alkaline hydrolysis using, for example, aqueous alcoholic sodium hydroxide or a lithium hydroxide/tetrahydrofuran/water mixture. These acids may be further converted to the compounds of formula I wherein Q represents halo, preferably chloro, by reaction with a suitable halogenating agent such as thionyl chloride or oxalyl chloride.

Particular examples of compounds according to the invention useful as acaricides and insecticides are those set out in Table I below. The compounds conform to the formula:

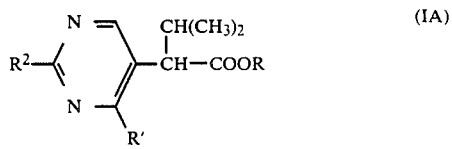

and the meaning of $R^1$, $R^2$ and R is given for each compound. R is defined as a group E-01 to E-31, the meanings of which are set out as follows:

E-01=3-phenoxybenzyl
E-02=1-cyano-1-(3-phenoxyphenyl)methyl
E-03=2-methyl-3-phenylbenzyl
E-04=4-methyl-2,3,5,6-tetrafluorobenzyl
E-05=4-allyl-2,3,5,6-tetrafluorobenzyl
E-06=N-3,4,5,6-tetrahydrophthalimidomethyl
E-07=1-ethynyl-1-(3-phenoxyphenyl)methyl
E-08=5-benzylfur-3-ylmethyl
E-09=6-phenoxypyrid-2-ylmethyl
E-10=1-cyano-1-(6-phenoxypyrid-2-yl)methyl
E-11=1[-(6-phenoxypyrid-2-yl)]ethyl
E-12=4-(prop-2-yn-1-yl)-2,3,5,6-tetrafluorobenzyl
E-13=4-(but-2-yn-1-yl)-2,3,5,6-tetrafluorobenzyl
E-14=4-(3-chloroprop-2-en-1-yl)-2,3,5,6-tetrafluorobenzyl
E-15=4-methoxymethyl-2,3,5,6-tetrafluorobenzyl
E-16=2-methoxy-4-methoxymethyl-3,5,6-trifluorobenzyl
E-17=4-benzyl-2,3,5,6-tetrafluorobenzyl
E-18=3-benzyl-4-fluorobenzyl
E-19=4-(3-trimethylsilylprop-2-yn-1-yl-2,3,5,6-tetrafluorobenzyl
E-20=4-(2-methylprop-2-en-1-yl)-2,3,5,6-tetrafluorobenzyl
E-21=4-ethoxy-2,3,5,6-tetrafluorobenzyl
E-22=4-trimethylsilyl-2,3,5,6-tetrafluorobenzyl
E-23=4-(but-2-en-1-yl)-2,3,5,6-tetrafluorobenzyl
E-24=4-(2-chloroprop-2-en-1-yl)-2,3,5,6-tetrafluorobenzyl
E-25=4-fluoro-3-phenoxybenzyl
E-26=2-chloro-6-fluorobenzyl
E-27=1-cyano-1-(3-benzyl-4-fluorophenyl)methyl
E-28=3-phenylaminobenzyl
E-29=4-(2,3-dichloroprop-2-en-1-yl)-2,3,5,6-tetrafluorobenzyl
E-30=pentafluorobenzyl
E-31=1-cyano-1-(4-fluoro-3-phenoxyphenyl)methyl

TABLE I

| Compound No. | $R^2$ | $R^1$ | R |
|---|---|---|---|
| I | $(CH_3)_3C$ | H | E-01 |
| II | $(CH_3)_3C$ | H | E-02 |
| III | $(CH_3)_3C$ | H | E-03 |
| IV | $(CH_3)_3C$ | H | E-04 |
| V | $(CH_3)_3C$ | H | E-05 |
| VI | $(CH_3)_3C$ | H | E-06 |
| VII | $(CH_3)_3C$ | H | E-07 |
| VIII | $(CH_3)_3C$ | H | E-08 |
| IX | $(CH_3)_3C$ | H | E-09 |
| X | $(CH_3)_3C$ | H | E-10 |
| XI | $(CH_3)_3C$ | H | E-11 |
| XII | $(CH_3)_3C$ | H | E-12 |
| XIII | $(CH_3)_3C$ | H | E-13 |
| XIV | $(CH_3)_3C$ | H | E-14 |
| XV | $(CH_3)_3C$ | H | E-15 |
| XVI | $(CH_3)_3C$ | H | E-16 |
| XVII | $(CH_3)_3C$ | H | E-17 |
| XVIII | $(CH_3)_3C$ | H | E-18 |
| XIX | $(CH_3)_3C$ | H | E-19 |
| XX | $(CH_3)_3C$ | H | E-20 |
| XXI | $(CH_3)_3C$ | H | E-21 |
| XXII | $(CH_3)_3C$ | H | E-22 |
| XXIII | $(CH_3)_3C$ | H | E-23 |
| XXIV | $(CH_3)_3C$ | H | E-24 |
| XXV | $(CH_3)_3C$ | H | E-25 |
| XXVI | $(CH_3)_3C$ | H | E-26 |
| XXVII | $(CH_3)_3C$ | H | E-27 |
| XXVIII | $(CH_3)_3C$ | H | E-28 |
| XXIX | $(CH_3)_3C$ | H | E-29 |
| XXX | $(CH_3)_3C$ | H | E-30 |
| XXXI | $(CH_3)_3C$ | Cl | E-05 |
| XXXII | $(CH_3)_3C$ | Cl | E-12 |
| XXXIII | $(CH_3)_3C$ | Cl | E-02 |

TABLE I-continued

| Compound No. | $R^2$ | $R^1$ | R |
|---|---|---|---|
| XXXIV | $(CH_3)_3C$ | Cl | E-10 |
| XXXV | $(CH_3)_3C$ | F | E-05 |
| XXXVI | $(CH_3)_3C$ | F | E-04 |
| XXXVII | $(CH_3)_3C$ | F | E-25 |
| XXXVIII | $(CH_3)_3CH$ | H | E-04 |
| XXXIX | $(CH_3)_3CH$ | H | E-05 |
| XL | $(CH_3)_3CH$ | H | E-30 |
| XLI | $(CH_3)_3CH$ | H | E-12 |
| XLII | $C_2H_5(CH_3)_2C$ | H | E-05 |
| XLIII | $C_2H_5(CH_3)_2C$ | H | E-12 |
| XLIV | $C_2H_5(CH_3)_2C$ | H | E-15 |
| XLV | $\begin{array}{c}CH_2\\ |\ \ \ \diagdown\\ \ \ \ \ \ \ \ \ CH-\\ |\ \ \ \diagup\\ CH_2\end{array}$ | H | E-05 |
| XLVI | $\begin{array}{c}CH_2\\ |\ \ \ \diagdown\\ \ \ \ \ \ \ \ \ CH-\\ |\ \ \ \diagup\\ CH_2\end{array}$ | H | E-12 |
| XLVII | $\begin{array}{c}CH_2\\ |\ \ \ \diagdown\\ \ \ \ \ \ \ \ \ CH-\\ |\ \ \ \diagup\\ CH_2\end{array}$ | H | E-18 |
| XLVIII | $\begin{array}{c}CH_2\ \ \diagdown\ \diagup\\ \ \ \ \ \ \ \ \ \ \ C\\ CH_2\ \diagup\ \diagdown CH_3\end{array}$ | H | E-05 |
| XLIX | $\begin{array}{c}CH_2\ \ \diagdown\ \diagup\\ \ \ \ \ \ \ \ \ \ \ C\\ CH_2\ \diagup\ \diagdown CH_3\end{array}$ | H | E-01 |
| L | $\begin{array}{c}CH_2\ \ \diagdown\ \diagup\\ \ \ \ \ \ \ \ \ \ \ C\\ CH_2\ \diagup\ \diagdown CH_3\end{array}$ | H | E-18 |
| LI | $\begin{array}{c}CH_2\ \ \diagdown\ \diagup\\ \ \ \ \ \ \ \ \ \ \ C\\ CH_2\ \diagup\ \diagdown CH_3\end{array}$ | H | E-12 |
| LII | $(CH_3)_3C$ | H | E-31 |

The insecticidally active compounds of the invention according to formula IA are esters, and may be prepared from the alkyl esters, acids and acid chlorides described above by conventional esterification processes, such as those described below, by way of example.

(a) An acid of formula:

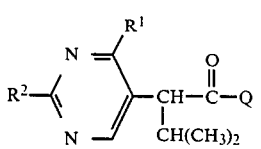

where Q represents the hydroxy group and $R^1$ and $R^2$ have any of the meanings given hereinabove, may be reacted directly with an alcohol of formula R-OH (III) where R has any of the meanings given hereinabove, the reaction preferably taking place in the presence of an acid catalyst, for example, dry hydrogen chloride, or a dehydrating agent, such as for example, dicyclohexyl carbodiimide.

(b) An acid halide of formula II where Q represents a halogen atom, preferably a chlorine atom, $R^1$ and $R^2$ have any of the meanings given hereinabove, may be reacted with an alcohol of formula III, the reaction preferably taking place in the presence of a base, for example, pyridine, alkali metal hydroxide or carbonate, or alkali metal alkoxide.

(c) An acid of formula II where Q represents the hydroxy group or, preferably, an alkali metal salt thereof, may be reacted with halide of formula Q'-R (IV) wherein Q' represents a halogen atom, preferably the chlorine atom, and R has any of the meanings given hereinabove, or with the quaternary ammonium salts derived from such halides with tertiary amines, for example pyridine, or trialkyl amines such as triethylamine.

(d) A lower alkyl ester of formula (II) where Q represents a lower alkoxy group containing up to six carbon atoms, preferably the methoxy or ethoxy group, and $R^1$ and $R^2$ have any of the meanings given hereinabove, is heated with an alcohol of formula III to effect a transesterification reaction. Preferably the process is performed in the presence of a suitable catalyst, for example, an alkali metal alkoxide, such as sodium methoxide, or an alkylated titanium derivative, such as tetramethyl titanate or tetraethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus the various optically active species may be obtained by fractional crystallisation of salts of the acids with optically active amines, for example (−)-α-methylbenzylamine, followed by regeneration of the optically pure acid. The optically pure isomeric form of the acid (or its equivalent acid chloride or ester) may then be reacted with the appropriate alcohol to produce a compound of formula IA in the form of an individually pure isomer thereof.

Where the compounds of Formula IA are formed as mixtures of four diastereoisomers, the two racemic isomer pairs can be separated by e.g., h.p.l.c. techniques, or, where the physical properties of the compounds are suitable, by selective crystallisation.

Further details of the processes which may be employed for the preparation of compounds of formula IA may be ascertained from the specific Examples set out hereinafter.

Many of the alcohols of formula R-OH which are useful in the preparation of the compounds of formula IA have been described previously. In particular the alcohols where R represents a substituted tetrafluorobenzyl moiety are described in U.S. Pat. Nos. 4,405,640 and 4,370,346 and published European patent application no. 0196156A1. Some of the alcohols are novel and have not been described in previously published documents, and their preparation is set out hereinafter in the Examples.

The compounds of formula IA may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula IA suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence at the locus of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-biollethrin, fenfluthrin, prallethrin and 5-benzyl-3-furylmethyl-(E)-(1R,3S)-2,2-dimethyl-3-(2-oxothiolan-3-ylidenemethyl carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones such as juvenile hormone, juvabione, or ecdysones;

(h) Pheromones;

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
Aonidiella spp. (scale insects)
Trialeuroides spp. (white flies)
*Blattella germanica* (cockroaches)
*Spodoptera littoralis* (cotton leaf worm)
*Heliothis virescens* (tobacco budworms)
*Chortiocetes terminifera* (locusts)
Diabrotica spp. (rootworms)
*Panonychus ulmi* (citrus mite)
*Nilaparvata lugens* (plant hoppers)
Agrotis spp. (cutworms)
*Chilo partellus* (maize stem borers)

The compounds of formula IA and compositions comprising them have shown themselves to be particularly useful in controlling acarine pests of plants such as red mites and rust mites as well as lepidopteran pests of cotton, for example Spodoptera spp. and Heliothis spp. Acarine pests of plants include for example Tetranychus spp. and Panonychus spp. The compounds of formula IA act against both motile stages (adults and nymphs) and ova. This combination of moticidal and ovicidal activity in the same compound is very desirable and avoids the necessity of having to use mixtures of compounds to achieve both effects, which is often the case with products used hitherto. A further advantage of the compounds is that at the rates of application used to control acarine pests effective control of insect pests present at the same locus, e.g. larval stages of lepidopterous and coleopterous pests, as well as hemipterous pests such as aphids, can often be achieved simultaneously. The compounds may also be used to combat pests which inhabit the soil, for example Diabrotica spp. They may also be useful in combating insect and acarine pests which infest domestic animals, such as *Lucilia sericata,* and ixodid ticks such as Boophilus spp., Ixodes sppl, Amblyomma spp., Rhipicephalus spp., and Dermaceutor spp. They may be effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic reasonance spectroscopy and infra red spectroscopy. In each case where a product is specifically named its spectral characteristics are consistent with the assigned structure.

In the Examples, Gas Liquid Chromatography (GLC) retention times were determined on a Hewlett Packard 5890 Gas Chromatograph, using a Chromopak, C.P. Sil 5 C.B. column of 12.5 m length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperature are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz and 60 MHz $^1$H NMR spectrometry were performed using Jeol FX 90 A and Jeol PMX60 spectrometers respectively.

$^{19}$F NMR spectrometry was performed on a Jeol FX90Q spectrometer at a frequency of 84.26 MHz. All NMR shift values are quoted in ppm relative to a standard (TMS or CFCl$_3$).

Molecular Ion (M+) peaks were determined on one of three mass spectrometers: Jeol DX303, Kratos MS80 or Hewlett Packard HP 5992.

EXAMPLE 1

This Example illustrates the preparation of 2,2-dimethylpropionamidine hydrochloride.

Dry hydrogen chloride gas (ca. 59 g) was passed through a solution of 2-cyano-2-methylpropane (86 g) in ethanol (60 cm$^3$) at 0° C. The solution was kept for 60 hours at the ambient temperature (ca. 20° C.), diluted with diethyl ether (1000 cm$^3$) and the precipitated 1-ethoxy-1-imino-2,2-dimethylpropane hydrochloride collected by filtration, washed on the filter with diethyl ether and dried. This was then slurried with ethanol (150 cm$^3$) and gaseous ammonia passed into the mixture at the ambient temperature until the solid was completely dissolved.

The mixture was kept at this ambient temperature for 40 hours, diluted with diethyl ether (500 cm$^3$) and the solid precipitate collected by filtration and dried to yield 2,2-dimethylpropionamidine hydrochloride (25.75 g), melting point 192°-194° C. A second crop (50.29 g) was obtained by evaporation of the filtrate.

Infra red (liquid paraffin): 3300, 3100, 1680, 1520 1230, 995, 980 cm$^{-1}$.

EXAMPLE 2

The Example illustrates the preparation of diethyl (RS)-formylsuccinate.

Ethanol (20 cm$^3$) was added portionwise to a suspension of finely divided sodium (10.0 g) in dry toluene (100 cm$^3$). On completion of the addition the mixture was heated for 3.5 hours at 80° C. To the resulting yellow suspension, cooled to 20° C., was added dropwise, over a period of 1 hour, a mixture of diethyl succinate (70.0 g) and ethyl formate (35.0 g), whilst the temperature of the mixture was maintained in the range 20 to 30° C. The mixture was kept at the ambient temperature for 16 hours after which water (100 cm$^3$) was added carefully.

The aqueous layer was separated, neutralised with 50% aqueous sulphuric acid, and extracted with diethyl ether. The ethereal extracts were washed with water, dried over anhydrous magnesium sulphate, and concentrated by evaporation of the solvent under reduced pressure. The residual liquid (66 g) was subjected to fractional distillation under reduced pressure to obtain the desired diethyl (RS)-formylsuccinate (46.0 g), boiling range 82 to 86° C./0.53 mmHg.

N.m.r spectroscopy indicated that the product exists as an approximately 1:1 mixture of keto and enol forms.

$^1$H NMR (CDCl$^3$)δ:1.10–1.40 (m,3H); 2.90 (d, J=7Hz, 1H); 3.05 (s,1H); 3.75 (t, J=7 Hz, 0.5H); 4.00–4.40 (m,4H); 7.10 (d, J=11 Hz, 0.5H); 9.92 (s, 0.5 H); 11.5 (d, J=11 Hz, 0.5H).

Infra red (liquid film): 3300, 2980, 1735, 1665, 1175, 1030 cm$^{-1}$.

EXAMPLE 3

This Example illustrates the preparation of 5-ethoxycarbonylmethyl-4-hydroxy-2-(2-methylprop-2-yl) pyrimidine.

A solution of sodium ethoxide obtained by dissolving sodium (6.9 g) in ethanol (120 cm$^3$) was added portionwise to a stirred suspension of 2,2-dimethylpropionamidine hydrochloride (41.0 g) in ethanol (150 cm$^3$). The precipitated sodium chloride was removed by filtration. Diethyl (RS)-formylsuccinate (60 g) was added dropwise to the stirred filtrate at the ambient temperature. After keeping the mixture for 16 hours it was heated to the reflux temperature for 1 hour, after which the solvent was removed by evaporation under reduced pressure to give a solid residue which was washed with petroleum ether (boiling range 60°-80° C.) to yield 5-ethoxycarbonylmethyl-4-hydroxy-2-(2methylprop-2-yl)pyrimide (40 g), melting point 98°-102° C. A further quantity (15 g) was recovered from the petroleum ether washings by evaporation of the solvent and column chromatographic purification of the residue using a silica column and eluting with a mixture (1:1 by volume) of ethyl acetate and petroleum ether (boiling range 60°-80° C.).

$^1$H NMR (CDCl$_3$)δ:1.27 (t, J=7Hz, 3H); 1.39 (s, 9H); 3.44 (s, 2H); 4.13 (q, J=7 Hz, 2H); 7.92 (s, $^1$H); 12.5 (bs, 1H).

Infra red (liquid paraffin): 3400, 1735, 1660, 1570, 1460, 1375, 1335, 1275, 1155, 1030, 980 cm$^{-1}$.

EXAMPLE 4

This Example illustrates the preparation of 4-chloro-5-ethoxycarbonylmethyl-2-(2-methylprop-2-yl) pyrimidine.

Phosphorus oxychloride (30 cm$^3$) was added portionwise to 5-ethoxycarbonylmethyl-4hydroxy-2-(2-methylprop-2-yl)-pyrimidine (15.0 g). An exothermic reaction occurred and the resultant mixture was poured onto ice. After neutralisation with sodium carbonate the mixture was extracted with ethyl acetate and the extracts washed with water and dried over anhydrous magnesium sulphate. Removal of the solvent by evaporation under reduced pressure yielded 4-chloro-5-ethoxycarbonylmethyl-2-(2-methylprop-2-yl)pyrimidine (11.35 g, oil, solidified on standing, m.p. 42°–44° C.).

$^1$H NMR (CDCl$_3$)δ:1.29 (t, J=7Hz, 3H); 1.40 (s, 9H); 3.71 (s, 2H); 4.20 (q, J=7Hz, 2H); 8.51 (s, 1H).

Infra red (liquid film): 2960, 1735, 1580, 1520, 1420, 1250, 1180, 1025, 880 cm$^{-1}$.

EXAMPLE 5

This Example illustrates the preparation of 5-ethoxycarbonylmethyl-2-(2-methylprop-2-yl)pyrimidine.

A mixture 4-chloro-5-ethoxycarbonylmethyl-2-(2-methylprop-2-yl)pyrimidine (18 g), toluene (180 cm$^3$), zinc dust (36 g) and 3 molar ammonium hydroxide solution saturated with sodium chloride (180 cm$^3$) was heated at 100° C. for 120 hours. After cooling and filtering to remove the solid component the organic phase was separated, the aqueous phase washed with ethyl acetate and the washings combined with the organic phase. After washing the organic phase with water and drying over anhydrous magnesium sulphate the solvents were removed by evaporation under reduced pressure and the residual oil (16 g) was subjected to purification by column chromatography using a silica column eluted with dichloromethane to yield 5-ethoxycarbonylmethyl-2-(2-methylprop-2-yl)pyrimidine (12 g) as a yellow oil.

$^1$H NMR (CDCl$_3$)δ:1.25 (t, J=7Hz, 3H); 1.40 (s, 9H); 3.55 (s, 2H); 4.2 (q, J=7Hz, 2H); 8.6 (s, 2H).

Infra red (liquid film): 2960, 1735, 1480, 1430, 1260, 1180, 1025 cm$^{-1}$.

EXAMPLE 6

This Example illustrates the preparation of ethyl (RS)-2-[2-(2-methylprop-2-yl)pyrimidin-5-yl]-3-methylbutyrate.

Lithium bis(trimethylsilyl)amide (10.8 cm$^3$ of a 1 molar solution in dry tetrahydrofuran) was added dropwise to a solution of 5-ethoxycarbonylmethyl-2-(2-methylprop-2-yl)-pyrimidine (1.2 g) in dry tetrahydrofuran (30 cm$^3$) maintained at −78° C., and the resultant solution stirred for 90 minutes at −78° C., after which 2-iodopropane (2.7 cm$^3$) was added dropwise and the mixture was allowed to warm to the ambient temperature. The mixture was poured into water and extracted with ethyl acetate, the extracts combined, washed with water, dried over anhydrous magnesium sulphate and concentrated by evaporation of the solvent under reduced pressure. The residual oil (1.48 g) was distilled under reduced pressure and ethyl (RS)-2-[2-(2-methylprop-2-yl)pyrimidin-5-yl]-3-methylbutyrate collected as a colourless oil, (0.9 g), boiling point 130° C./0.08 mmHg.

$^1$H NMR (CDCl$_3$)δ:0.8, 1.05 (2d, J=7Hz, 6H); 1.25 (t, J=7 Hz, 3H); 1.4 (s, 9H); 2.2–2.5 (m, 1H); 3.1 (d, J=9Hz, 1H); 4.2 (q, J=7Hz, 2H); 8.6 (s, 2H).

Infra red (liquid film):2960, 1725, 1585, 1430, 1180, 1150, 1020 cm$^{-1}$.

EXAMPLE 7

This Example illustrates the preparation of ethyl (RS)-2-[2-(2-methylprop-2-yl)-4-chloropyrimidin-5-yl]-3-methylbutyrate.

4-chloro-5-ethoxycarbonylmethyl-2-(2-methylprop-2-yl)pyrimidine was reacted with 2-iodo-propane in the presence of lithium bis(trimethylsilyl)amide according to the procedure illustrated in example 6, to give ethyl (RS)-2-[2-(2-methylprop-2-yl)-4-chloropyrimidin-5-yl]-3-methylbutyrate.

$^1$H NMR (CDCl$_3$)δ:0.8, 1.1 (2d, 6H); 1.25 (t, 3H); 1.4 (s, 9H); 2.4 (m, 1H); 3.8 (d, 1H); 4.2 (q, 2H); 8.8 (s, 1H).

Infra red (liquid film): 2980, 1740, 1425 and 1190 cm$^{-1}$.

GLC retention time: 4.58 minutes.

EXAMPLE 8

This Example illustrates the preparation of ethyl (RS)-2-[2-(2-methylprop-2-yl)-4-fluoropyrimidin-5-yl]-3-methylbutyrate.

A stirred suspension of dry potassium fluoride (1.41 g) and ethyl (RS)-2-[2-(2-methylprop-2-yl)-4-chloropyrimidin-5-yl]-3-methylbutyrate (1.88 g) in dry sulpholane (14 cm$^3$) in the presence of 18-crown-6 (0.38 g) was heated to 150° C. for a period of 24 hours, under an atmosphere of dry nitrogen. After cooling to the ambient temperature (ca. 22° C.), the reaction mixture was poured into water, and extracted into ethyl acetate. The organic layer was washed with water and brine, dried and the solvent evaporated under reduced pressure. The residual brown liquid was purified by column chromatography on silica gel, using dichloromethame as eluent, to give ethyl (RS)-2-[2-(2-methylprop-2-yl)-4-fluoropyrimidin-5-yl]-3-methylbutyrate (0.8 g) as an orange liquid.

$^1$H NMR (CDCl$_3$)δ:0.8, 1.05 (2d, 6H); 1.3 (t, 3H); 1.4 (s, 9H); 2.4 (m, 1H); 3.55 (d, 1H); 4.2 (q, 2H); 8.8 (d, 1H).

GLC retention time: 3.82 minutes.

EXAMPLE 9

By a procedure similar to that described in Example 1, the following compounds were prepared from the appropriate starting nitriles; where the starting materials are not readily available, their preparation is described in Examples 16 and 17. In each case below, the incubation time with hydrogen chloride (to produce the intermediate iminoether) and subsequent incubation time with ammonia (to produce the amidine) are noted where they differ from those recorded in Example 1.

(i) 2-Methylpropionamidine hydrochloride from 2-methylpropionitrile

Hydrogen chloride reaction time: 18 hours (initial warming to 30° C. required to initiate reaction)

Ammonia reaction time: 48 hours.

Infra red (liquid paraffin): 3300, 3100, 1680, 1520 cm$^{-1}$.

(ii) Cyclopropanecarboxamidine hydrochloride from cyclopropanecarbonitrile.

Hydrogen chloride reaction time: 6 days.

Ammonia reaction time: 16 hours.
Melting point: 55°–58° C.
$^1$H NMR (CDCl$_3$)δ:0.85 (m); 1.2 (m); 1.7 (m).
Infra red (liquid paraffin): 3400, 3200, 1650, 1460, 1380, 1310, 1150, 1040, 940 cm$^1$.
(iii) 2,2-Dimethylbutyramidine hydrochloride from 2,2-dimethylbutyronitrile.
Melting point 128°–129° C.
Infra red (liquid paraffin): 3350–2630, 1670, 1510, 1460, 1380, 1300, 1210, 1085 cm$^{-1}$.
(iv) 1-Methylcyclopropanecarboxamidine hydrochloride from 1-methylcyclopropanecarbonitrile.
Hydrogen chloride reaction time: 1 hour.
Ammonia reaction time: 48 hours.
$^1$H nmr (CDCl$_3$) δ:0.84 (m, 2H); 1.16 (m, 2H); 1.26 (s, 3H); 8.40–9.00 (broad, 3H).
Infra red (liquid paraffin): 3200 (broad), 1670, 1530, 1085, 960, 890 cm$^{-1}$.

EXAMPLE 10

This example illustrates the steps involved in the preparation of ethyl (RS)-4-dimethylamino-3-formyl-2-(1-methylethyl)-3-butenoate, ethyl (RS)-4-ethoxy-3-formyl-2-(1-methylethyl)-3-butenoate and mixtures thereof.

(i) Preparation of diethyl 2-(1-methylethyl)-2-(2,2-diethoxyethyl)-malonate. (Reference Bull. Soc. Chim. France, 1965, p 1761).

Sodium hydride (4.8 g of a 50% dispersion in oil) was washed free of oil with petroleum ether of boiling range 40°–60° C., and suspended in dry dimethylformamide; the suspension was cooled to 0° C. by external cooling. A solution of diethyl 2-(1-methylethyl)malonate (21.2 g) in dry dimethylformamide (25 cm$^3$) was added in portions to the suspension and the reaction mixture was stirred at 10° C. for 15 minutes, whereafter no further evolution of hydrogen could be detected. A solution of bromoacetaldehyde diethylacetal (19.7 g - commercially available from Aldrich Chemical Company Limited, Gillingham, England) in dimethylformamide (25 cm$^3$) was added to the reaction mixture to give a red-brown solution, which was then heated at 120°–130° C. for 20 hours with stirring. After cooling the reaction mixture to 0° C., an ice/water mixture (total volume 1000 cm$^3$) was added cautiously. The product was extracted with diethyl ether (3×250 cm$^3$) and the combined organic layers washed with water (2×300 cm$^3$), dried over anhydrous magnesium sulphate and concentrated by evaporation of the solvent under reduced pressure. The residual liquid was subjected to fractional distillation through a short Vigreux column to give diethyl 2-(1-methyl-ethyl)-2-(2,2-diethoxyethyl)malonate (10.5 g), boiling point 94°–98° C./0.1 mmHg.

$^1$H NMR (CDCl$_3$)δ: 1.0 (d, 6H); 1.2 (t, 6H); 1.3 (t, 6H); 2.25 (d, 2H); 2.3 (m, 1H); 3.4–3.75 (m, 4H); 4.2 (m, 4H); 4.65 (m, 1H).
Infra red (liquid film): 2990, 1730, 1230, 1120, 1070 cm$^{-1}$.

(ii) Preparation of ethyl (RS)-4,4-diethoxy-2-(1- methylethyl)butyrate.

Diethyl 2-(1-methylethyl)-2-(2,2-diethoxy-ethyl)malonate (60 g) was added to dimethyl sulphoxide (450 cm$^3$) containing potassium acetate (37 g) and water (6.8 cm$^3$). The mixture was stirred under nitrogen and heated to 130°–140° C. for 18 hours. Analysis by gas liquid chromatography indicated that the reaction was 40% complete. The reaction temperature was increased to 160°–170° C. and heating continued for a further 18 hours.

The reaction mixture was cooled to room temperature and diluted with water (3000 cm$^3$). The product was extracted using diethyl ether (3×800 cm$^3$) and the combined organic layers were washed with water (3×800 cm$^3$) and dried over anhydrous magnesium sulphate. The solvent was evaporated under reduced pressure to give a brown liquid. Fractional distillation of the residue gave ethyl (RS)-4,4-diethoxy-2-(1-methylethyl)butyrate (31.8 g) as a pale yellow liquid, boiling point 68°–70° C./0.2 mmHg.

1H NMR (CDCl$_3$)δ0.9 (d, 6H); 1.0 (m, 9H); 1.75 (m, 1H); 1.8–2.05 (m, 2H); 2.15 (m, 1H); 3.4–3.7 (m, 4H); 4.05–4.2 (m, 2H); 4.45 (m, 1H).
Infra red (liquid film):2990, 1730, 1375, 1180, 1120, 1060 cm$^{-1}$.

This compound may also be prepared by the methods described in Chemical Abstracts, 59, 5012g (1963) and 51 12086c (1957).

(iii) Preparation of ethyl (RS)-4-dimethylamino-3-formyl-2-(1-methylethyl)-3-butenoate, ethyl (RS)-4-ethoxy-3-formyl-2-(1-methylethyl)-3-butenoate and mixtures thereof.

To dry dimethylformamide (4.64 cm$^3$) was added dropwise at 5° C., phosphorous oxychloride (5.50 cm$^3$). This gave initially a viscous solution which then solidified. To this was added 1,2-dichloroethane (10 cm$^3$) and the reaction mixture stirred at 60° C. for 45 minutes to form the Vilsmeyer - Haack reagent.

A solution of ethyl (RS)-4,4-diethoxy-2-(1-methylethyl)butyrate (5 g) in 1,2-dichloroethane (10 cm$^3$) was added dropwise to the reaction mixture, which was then heated for a further 1 hour at 60° C.

The reaction mixture was sampled by adding an aliquot to solid potassium carbonate, diluting with water, and heating for a 5 minutes at 50°–60° C. An extract using ethyl acetate as solvent was analysed by gas liquid chromatography, which indicated 30% completion of reaction.

The reaction mixture was heated for a further 1 hour at 70° C., allowed to cool to room temperature, then reheated for a further 1 hour at 70° C. The reaction mixture was cooled to 0° C. and cautiously added to an excess of solid potassium carbonate. The slurry was cautiously diluted with ice/water and the mixture heated on a steam bath for 10 minutes. The mixture was cooled to room temperature and saturated sodium chloride solution added. The product was extracted with ethyl acetate (2×750 cm$^3$), dried over anhydrous magnesium sulphate and the solvent was evaporated under reduced pressure. The residual brown liquid was placed under vacuum (0.5–1.0 mmHg) and heated to 50° C. to remove volatile impurities.

The product was obtained as a brown liquid (3.4 g) and was used without further purification.

Analysis of the product by gas chromatography/mass spectroscopy showed the product to contain 68% ethyl (RS)-4-dimethylamino-3-formyl-2-(1-methyl ethyl)-3-butencate (I), 12% ethyl (RS)-4-ethoxy-3-formyl-2-(1-methylethyl)-3-butenoate (II) and 17.5% 3-(1-methylethyl)-5-hydroxy-tetrahydrofuran-2-one (III) as an impurity. Ratios of I to II were found to vary according to reaction conditions and isolation procedures, but all mixtures were found to be satisfactory for further conversion to derivatives as described in the remaining examples.

Molecular ion (Product I): 227.

Molecular ion (Product II): 228.
Molecular ion (Product III): 144.

EXAMPLE 11

This Example illustrates the preparation of ethyl (RS)-2-[2-(2-methylprop-2-yl)pyrimidin-5-yl]-3-methylbutyrate.

2,2-dimethylpropionamidine hydrochloride (0.14 g), prepared according to Example 1, was added to a solution of a 4:3 mixture of ethyl (RS)-4-dimethylamino-3-formyl-2-(1-methylethyl)-3-butenoate and ethyl (RS)-4-ethoxy-3-formyl- 2-(1-methylethyl)-3-butenoate (0.2 g), prepared according to the method of Example 10, in ethanol (2 cm$^3$). A solution of sodium methoxide (0.06 g) in ethanol (1 cm$^3$) was added to the stirred mixture, which was then heated at the reflux temperature for 2 hours. After cooling, the ethanol was evaporated under reduced pressure. The residual oil was purified by column chromatography on a silica gel support (Merck 7729), using dichloromethane, followed by dichloromethane containing 2% by volume ethyl acetate, as eluent, to give ethyl (RS)-2-[2-(2-methylprop-2-yl)pyrimidin-5-yl]-3-methylbutyrate (0.068 g) as a pale yellow oil.

The NMR and Infra Red spectra of the product were identical with those recorded for the product of Example 6.

EXAMPLE 12

The following compounds were prepared from the appropriate amidine hydrochlorides by a procedure similar to that described in Example 11. Preparation of amidine hydrochlorides is described in Examples 1 and 9.

(i) Ethyl (RS)-2-[2-(1-methylethyl)pyrimidin-5-yl]-3-methylbutyrate from 2-methylpropionamidine hydrochloride.

$^1$H NMR (CDCl$_3$)δ: 0.76 (d, 3H); 1.06 (d, 3H); 1.28 (t, 3H); 1.36 (d, 6H); 2.34 (m, 1H); 3.12 (m, 2H); 4.16 (q, 2H); 8.68 (s, 2H).

Molecular ion : 250

(ii) Ethyl (RS)-2-(2-cyclopropylpyrimidin-5-yl)-3-methylbutyrate from cyclopropanecarboxamidine hydrochloride.

$^1$H NMR (CDCl$_3$)δ: 0.76 (d, 3H ; 1.16 (m, 10 H); 2.24 (m, 2H); 3.10 (d, 1H); 4.12 (q, 2H); 8.56 (s, 2H).

Molecular ion : 248.

(iii) Ethyl (RS)-2-[2-(1-methylcyclopropyl)pyrimidin-5-yl]-3-methylbutyrate from 1-methylcyclopropanecarboxamidine hydrochloride.

$^1$H NMR (CDCl$_3$)δ: 1.04 (m, 13H); 1.60 (s, 3H); 2.36 (m, 1H); 3.21 (d, 1H); 4.12 (q, 2H); 8.58 (s, 2H).

Molecular ion : 262.

(iv) Ethyl (RS)-2-[2-(1,1-dimethylprop-1-yl)pyrimidin-5-yl]-3-methylbutyrate from 2,2-dimethylbutyramidine hydrochloride.

$^1$H NMR (CDCl$_3$)δ: 1.00 (m, 18H); 1.80 (q, 2H); 2.34 (m, 1H); 3.16 (d, 1H); 4.16 (q, 2H); 8.68 (s, 2H).

Molecular ion : 278.

EXAMPLE 13

This Example illustrates two alternative routes to the esters of the invention - method A and method B.

METHOD A (i) Preparation of (RS)-2-[2-(2-methylprop-1-yl)pyrimidin-5-yl]-3-methylbutyric acid.

A mixture of ethyl (RS)-2-[2-(2-methylprop-2-yl)-pyrimidin-5-yl]-3-methylbutyrate (5.4 g), lithium hydroxide monohydrate (2.16 g), tetrahydrofuran (108 cm$^3$) and water (108 cm$^3$) was heated at 80° C. for 8 hours. After cooling and pouring into dilute hydrochloric acid, the mixture was extracted with ethyl acetate, the extracts combined, washed with water, dried over anhydrous magnesium sulphate and concentrated by evaporation of the solvent under reduced pressure.

The residual oil was triturated with petroleum ether (boiling range 40° to 60° C.) to yield (RS)-2-[2-(2-methyprop-2-yl)pyrimidin-5-yl]-3-methylbutyric acid (2.6 g) as a white solid.

$^1$H nmr (CDCl$_3$)δ: 0.8, 1.1 (2d, J=7Hz, 6H); 1.4 (s,9H); 2.0-2.5 (m, 1H); 3.2 (d,J=9Hz, 1H); 8.6 (s, 2H); 9.5 (s, 1H).

Infra red (liquid paraffin): 2600, 1710, 1550, 1470, 1375, 1305, 720, 650 cm$^{-1}$.

(ii) Preparation of (RS)-1-ethynyl-1-3-phenoxyphenyl)-methyl (RS)-2-[2-(2-methylprop-2-yl)pyrimidin-5-yl]-3-methylbutyrate (Compound VII)

A solution of N,N'-dicyclohexylcarbodiimide (0.2 g) in dichloromethane (5 cm$^3$) was added to a stirred mixture of (RS)-2-[2-(2-methylprop-2-yl)pyrimidin-5-yl]-3-methylbutyric acid (0.26 g), (RS)-α-ethynyl-3-phenoxybenzyl alcohol (0.224 g), 4-dimethylaminopyridine (0.02 g) and dry dichloromethane (5 cm$^3$) and the resultant mixture stirred for 2 hours. The precipitate which formed was removed by filtration and the filtrate concentrated by evaporation of the solvent under reduced pressure. The residual oil was purified by column chromatography using a silica column eluted with a mixture of ethyl acetate (1 part by volume) and petroleum ether (boiling range 60° to 80° C., 1 part by volume) to yield (RS)-1-ethynyl-1-(3-phenoxyphenyl)methyl (RS)-2-[2-(2-methylprop-2-yl)-pyrimidin-5-yl]-3-methylbutyrate (0.4g), as a mixture of diastereoisomers.

$^1$H nmr (CDCl$_3$)δ: 0.70, 0.75, 0.95, 1.00 (4d, J=7Hz, 6H); 1.41 (s, 9H); 2.30 (m, 1H); 2.60, 2.55 (2d, J=2Hz, 1H); 3.19 (d, J=9Hz, 1H); 6.39, 6.35 (2d, J=2Hz, 1H;) 6.80-7.50 (m, 9H); 8.60 (s, 2H)

Infra red (liquid film): 3280, 2960, 2920, 2890, 2120, 1740, 1585, 1540, 1480, 1430, 1245, 1210, 1140, 690 cm$^{-1}$.

METHOD B

Preparation of 3-phenoxybenzyl (RS)-2-[2-(1-methylcyclopropyl)pyrimidin-5-yl]-3-methylbutyrate (Compound XLIX).

A catalytic amount of titanium IV ethoxide was added to a solution of ethyl (RS)-2-[2-(1-methylcycloprop-1-yl)pyrimidin-5-yl]-3-methylbutyrate (0.2 g) and 3-phenoxybenzyl alcohol (0.305 g) in dry toluene (6 cm$^3$), and the reaction mixture was stirred at the reflux temperature for 18 hours. The progress of the reaction was monitored by withdrawing samples from the reaction vessel partitioning between ethyl acetate and water, and analysing the organic phase by gas liquid chromatography. In examples where the reaction was found to be incomplete after 18 hours, it was found effective to cool the mixture, evaporate the solvent and ethanol formed in the reaction under reduced pressure, redissolve the residue in toluene and add a further catalytic amount of titanium IV ethoxide; the reaction mixture was then reheated to the reflux temperature and the reaction continued until completion.

On completion of the reaction, the volatile components were evaporated under reduced pressure, and the residue partitioned between ethyl acetate and water. The organic layers were combined, dried over anhydrous magnesium sulphate and evaporated under reduced pressure. The residual oil was purified by column chromatography on a silica gel support, eluting with dichloromethane containing 2% by volume ethyl acetate, to give 3-phenoxybenzyl (RS)-2-[2-(1-methylcyclopropyl)pyrimidin-5-yl]-3-methylbutyrate.

$^1$H NMR (CDCl$_3$)δ: 0.75 (d, 3H); 0.92 (m, 2H); 0.98 (d, 3H); 1.36 (m, 2H); 1.58 (s, 3H); 2.34 (m, 1H); 3.18 (m, 1H); 5.08 (q, 2H); 7.16 (m, 9H); 8.54 (s, 2H).

Infra Red (liquid film): 2970, 1735, 1590, 1545, 1445, 1370, 1260, 1020 cm$^{-1}$.

EXAMPLE 14

The following compounds were prepared from the appropriate starting materials by either Method A or Method B of Example 13. Physical characteristics of the intermediate acids of Method A not previously described in these Examples are given in Example 15. The preparation of those alcohol intermediates which were not readily available is described in Examples 18 to 25.

(i) 3-Phenoxybenzyl (RS)-2-[2-(2-methylprop-2-yl)pyrimidin-5-yl]-3-methylbutyrate (Compound I) by Method A.

$^1$H NMR (CDCl$_3$)δ: 0.75, 1.00 (d, J=7Hz, 6H); 1.41 (s, 9H); 2.30 (m, 1H); 3.15 (d, J=9Hz, 1H); 5.08 (s, 2H); 6.80–7.40 (m, 9H); 8.64 (s, 2H).

Infra red (liquid film): 2960, 1735, 1580, 1480, 1425, 1250, 1210, 1140 cm$^{-1}$.

(ii) (RS-1-Cyano-1-(3-phenoxyphenyl)methyl (RS)-2-[2-(2-methylprop-2-yl)pyrimidin-5-yl]-3-methylbutyrate (Compound II) by Method A.

$^1$H NMR (CDCl$_3$)δ: 0.95–1.20 (4d, J=7Hz, 6H); 1.33 (s, 9H); 2.30 (m, 1H); 3.30 (d, J=9Hz, 1H); 6.35, 6.40 (2s, 1H); 7.00–7.60 (m, 9H); 8.55, 8.57 (2s, 2H).

Infra red (liquid film) : 2960, 1740, 1580, 1480, 1430, 1240, 685 cm$^{-1}$.

(iii) 2-Methyl-3-phenylbenzyl (RS)-2-[2-(2-methylprop-2-yl)pyrimidin-5-yl]-3-methylbutyrate (Compound III) by Method A.

$^1$H NMR (CDCl$_3$)δ: 0.75, 1.00 (2d, J=7Hz, 6H); 1.41 (s, 9H); 2.13 (s, 3H); 2.30 (m, 1H); 3.20 (d, J=9Hz, 1H); 5.19 (s, 2H); 7.20–7.45 (m, 8H); 8.67 (s, 2H).

Infra red (liquid film): 2960, 1735, 1660, 1585, 1480, 1430, 1175, 1145, 760, 700 cm$^{-1}$.

(iv) 2,3,5,6-Tetrafluoro-4-methylbenzyl (RS)-2-[2-(2-methylprop-2-yl)pyrimidin-5-yl]-3-methylbutyrate (Compound IV) by Method A.

$^1$H NMR (CDCl$_3$)δ: 0.75, 1.00 (2d, J=7Hz, 6H); 1.41 (s, 9H); 2.25 (m, 1H); 2.28 (t, J=2Hz, 3H); 3.18 (d, J=9Hz, 1H); 5.20 (bs, 2H); 8.67 (s, 2H).

Infra red (liquid film): 1740, 1490, 1430, 1285 cm$^{-1}$.

(v) 4-(Prop-2-en-1-yl)-2,3,5,6-tetrafluorobenzyl (RS)-2-[2-(2-methylprop-2-yl)pyrimidin-5-yl]-3-methylbutyrate (Compound V) by Method A.

$^1$H NMR (CDCl$_3$)δ: 0.78, 1.05 (2d, J=7Hz, 6H); 1.41 (s, 9H); 2.30 (m, 1H); 3.18 (d, J=9Hz, 1H); 3.45 (bd, J=6.5Hz, 2H); 4.80–5.25 (m, 4H); 5.60–6.10 (m, 1H); 8.65 (s, 2H)

Infra red (liquid film): 2960, 1740, 1490, 1430 cm$^{-1}$.

(vi) N-(3,4,5,6-tetrahydrophthalimido)methyl (RS)-2-2-(2-methylprop-2-yl)pyrimidin-5-yl]-3-methylbutyrate (Compound VI) by Method A.

$^1$H NMR (CDCl$_3$)δ: 0.75, 1.00 (2d, 6H); 1.41 (s, 9H); 1.78 (m, 4H); 2.35 (m, 5HH); 3.10 (d, J=9Hz, 1H); 5.50 (d, J=14Hz, 1H); 5.58 (d, J=14Hz, 1H); 8.62 (s, 2H)

Infra red (liquid film): 2960, 1730, 1590, 1550, 1480, 1430, 1140 cm$^{-1}$.

(vii) 5-Benzylfur-3-ylmethyl (RS)-2-[2-(2-methylprop-2-yl)-pyrimidin-5-yl]-3-methylbutyrate (Compound VIII) by Method A.

$^1$H NMR (CDCl$_3$)δ: 0.75, 1.00 (2d, J=7Hz, 6H); 1.41 (s, 9H); 2.30 (m, 1H); 3.17 (d, J=9Hz, 1H); 4.92 (bs, 2H); 6.00 (bs, 1H); 7.20–7.38 (m, 6H); 8.65 (s, 2H).

Infra red (liquid film): 2960, 1735, 1590, 1550, 1430, 1175, 1150, 950 cm$^{-1}$.

(viii) 6-phenoxypyrid-2-ylmethyl (RS)-2-[2-(2-methylprop-2-yl)pyrimidin-5-yl]-3-methylbutyrate (Compound IX) by Method A.

$^1$H NMR (CDCl$_3$)δ: 0.75, 1.00 (2d, J=7Hz, 6H); 1.41 (s, 9H); 2.30 (m, 1H) 3.25 (d, J=9Hz, 1H); 5.08 (s, 2H); 6.70–7.70 (m, 8H); 8.66 (s, 2H).

Infra red (liquid film): 2960, 1735, 1590, 1570, 1490, 1480, 1450, 1430, 1150, 690 cm$^{-1}$.

(ix) (RS)-1-Cyano-1-(6-phenoxypyrid-2-yl)methyl (RS)-2-[2-(2-methylprop-2-yl)pyrimidin-5-yl]-3-methylbutyrate (Compound X) by Method A.

$^1$H NMR (CDCl$_3$)δ: 0.75–1.00 (4d, J=7Hz, 6H); 1.41 (s, 9H); 2.30 (m, 1H); 3.28, 3.30 (2d, J=7Hz, 1H); 6.32, 6.34 (2s, 1H); 6.80–7.80 (m, 8H); 8.63 (8, 2H).

Infra red (liquid film): 2960, 1735, 1590, 1490, 1440 cm$^{-1}$.

(x) (RS)-1-[1-(6-phenoxypyrid-2-yl)]ethyl (RS)-2-[2-(2-methylprop-2-yl)pyrimidin-5-yl]-3-methylbutyrate (Compound XI) by Method A.

$^1$H NMR (CDCl$_3$)δ: 0.75–1.15 (4d, J=7Hz, 6H); 1.41 (s, 9H); 1.45, 1.55 (2d, J=6.5Hz, 3H); 2.30 (m, 1H); 3.23 (d, J=9Hz, 1H); 5.78, 5.80 (2q, J=6.5Hz, 1H); 6.60–7.80 (m, 8H); 8.63 (s, 2H).

Infra red (liquid film): 2960, 1735, 1590, 1570, 1440, 1255 cm$^{-1}$.

(xi) 4-(Prop-2-yn-1-yl)-2,3,5,6-tetrafluorobenzyl (RS)-2-[2-(2-methylprop-2-yl)pyrimidin-5-yl]-3-methylbutyrate (Compound XII) by Method A.

$^1$H NMR (CDCl$_3$)δ: 0.95, 1.05 (2d, 6H); 1.4 (s, 9H); 2.1 (t, 1H); 2.2–2.5 (m, 1H); 3.25 (d, 1H); b 3.65 (d, 2H); 5.25 (s, 2H); 8.6 (s, 2H).

Infra red (liquid film): 3320, 2965, 1745, 1490, 1435 1280, 1150, 1050, 860 cm$^{-1}$.

(xii) 4-(But-2-yn-1-yl)-2,3,5,6-tetrafluorobenzyl (RS)-2-[2-(2-methylprop-2-yl)pyrimidin-5-yl]-3-methylbutyrate (Compound XIII) by Method A.

$^1$H NMR (CDCl$_3$)δ: 0.8, 1.05 (2d, 6H); 1.4 (s, 9H); 1.8 (t, 3H); 2.35 (m, 1H); 3.2 (d, 1H); 3.6 (broad s, 2H); 5.2 (ABq, 2H); 8.6 (s, 2H); 8.6 (s, 2H).

Infra red (liquid film): 1750, 1495, 1440, 1285, 1150 1050 cm$^{-1}$.

GLC retention time : 9.25 minutes.

(xiii) Z-4-(3-chloroprop-2-en-1-yl)-2,3,5,6-tetrafluorobenzyl (RS)-2-[2-(2-methylprop-2-yl)pyrimidin-5-yl]-3-methylbutyrate (Compound XIV) by Method A.

$^1$H NMR (CDCl$_3$)δ:0.8, 1.05 (2d, 6H); 1.4 (s, 9H); 2.35 (m, 1H); 3.2 (d, 1H); 3.65 (d, 2H); 5.2 (ABq, 2H); 5.8 (dt, 1H); 6.2 (d, 1H); 8.6 (s, 2H).

Infra red (liquid film): 1750, 1490, 1440, 1300, 1150, 1055 cm$^{-1}$.

GLC retention time : 9.63 minutes.

(xiv) 4-(Methoxymethyl)-2,3,5,6-tetrafluorobenzyl (RS)-2-[2-(2-methylprop-2-yl)pyrimidin-5-yl]-3-methylbutyrate (Compound XV) by Method A.

$^1$H NMR (CDCl$_3$)δ: 0.75, 1.05 (2d, 6H); 1.4 (s, 9H); 2.3 (m, 1H); 3.2 (d, 1H); 3.4 (s, 3H); 4.6 (broad s, 2H); 5.25 (s, 2H); 8.6 (s, 2H).

Infra red (liquid film): 1745, 1495, 1290, 1150, 1115, 1060 cm$^{-1}$.

$^{19}$F NMR (CDCl$_3$)δ(relative to CFCl$_3$) : −143.516.

GLC retention time : 8.7 minutes.

(xv) 2-Methoxy-4-(methoxymethyl)-3,5,6-trifluorobenzyl (RS)-2-[2-(2-methylprop-2-yl)pyrimidin-5-yl]-3-methylbutyrate (Compound XVI) by Method A.

$^1$H NMR (CDCl$_3$)δ: 0.75, 1.05 (2d, 6H); 1.4 (s, 9H); 2.2–2.4 (m, 1H); 3.2 (d, 1H); 3.4 (s, 3H); 3.8 (d, 3H); 4.55 (t, 2H); 5.2 (broad, s,2H); 8.6 (s, 2H).

$^{19}$F NMR (CDCl$_3$)δ(relative to CFCl$_3$) : −137.193 (d); −144.247 (m); 145.462 (d).

Infra red (liquid film): 1745, 1490, 1440, 1285, 1155, 1115, 1070, 990 cm$^{-1}$.

GLC retention time : 9.42 minutes.

(xvi) 4-Benzyl-2,3,5,6-tetrafluorobenzyl (RS)-2-[2-(2-methylprop-2-yl)pyrimidin-5-yl]-3methybutyrate (Compound XVII) by Method A.

$^1$H NMR (CDCl$_3$)δ: 0.8, 1.05 (2d, 6H); 1.4 (s, 9H); 2.35 (m, 1H); 3.2 (d, 1H); 4.05 (s, 2H); 5.2 (ABq, 2H); 7.2–7.3 (m, 5H); 8.6 (s, 2H).

Infra red (liquid film) : 1745, 1490, 1440, 1280, 1150, 1050, 1980, 705 cm$^{-1}$.

GLC retention time : 11.27 minutes.

(xvii) 3-Benzyl-4-fluorobenzyl (RS)-2-[2-(2-methylprop-2-yl)pyrimidin-5-yl]-3-methylbutyrate (Compound XVIII) by Method A.

$^1$H NMR (CDCl$_3$) 0.8, 1.0(2d,6H); 1.4 (s, 9H); 2.2–2.4 (m, 1H); 3.2 (d, 1H); 4.0 (d, 2H); 5.05 (ABq, 2H); 7.0–7.4 (m, 8H); 8.65 (s, 2H).

$^{19}$F NMR (CDCl$_3$)δ(relative to CFCl$_3$) : −118.517 (s).

Infra red (liquid film) : 1740, 1505, 1440, 1250, 1180 1155, 1115, 820, 730, 700 cm$^{-1}$.

GLC retention time : 11.26 minutes.

(xviii) 4-(3-(Trimethylsilyl)prop-2-yn-1-yl)-2,3,5,6-tetrafluorobenzyl (RS)-2-[2-(2-methylprop-2-yl)pyridimin-5-yl]-3-methylbutyrate (Compound XIX) by Method A.

$^1$H NMR (CDCl$_3$)δ: 0.2 (s, 9H); 0.8, 1.05 (2d, 6H); 1.4 (s, 9H); 2.3 (m, 1H); 3.2 (d, 1H); 3.65 (broad S, 2H); 0.2 (ABq, 2H); 8.6 (s, 2H).

$^{19}$F NMR (CDCl$_3$)δ(relative to CFCl$_3$) : −143.466 (s).

Infra red (liquid film) : 1745, 1495, 1440, 1255, 1240, 1150, 1050, 850 cm$^{-1}$.

GLC retention time : 9.79 minutes.

(xix) 4-(2-methylprop-2-en-1-yl)-2,3,5,6-tetrafluorobenzyl (RS)-2-[2-(2-methylprop-2-yl)pyrimidin-5-yl]-3-methylbutyrate (Compound XX) by Method A $^1$H NMR (CDCl$_3$)δ: 0.8, 1.05 (2d, 6H); 1.4 (s, 9H); 1.8 (s, 3H); 2.35 (m, 1H); 3.2 (d, 1H); 3.4 (s, 2H); 4.6 (s, 1H); 4.85 (s, 1H); 5.2 (ABq, 2H); 8.6 (s, 2H).

Infra red (liquid film) : 1745, 1490, 1430, 1285, 1145, 1050 cm$^{-1}$.

GLC retention time : 8.84 minutes.

(xx) 4-Ethoxy-2,3,5,6-tetrafluorobenzyl (RS)-2-[2-(2-methylprop-2-yl)pyrimidin-5-yl]-3-methylbutyrate (Compound XXI) by Method A $^1$H NMR (CDCl$_3$)δ: 0.8, 1.05 (2d, 6H); 1.4 (s, 9H); 1.4 (t, 3H); 2.35 (m, 1H); 3.2 (d, 1H); 4.3 (q, 2H); 5.2 (ABq, 2H); 8.6 (s, 2H).

Infra red (liquid film) : 1740, 1590, 1500, 1435, 1390, 1145, 940 cm$^{-1}$.

GLC retention time : 8.42 minutes.

(xxi) 4-(Trimethylsilyl)-2-3,5,6-tetraflurobenzyl (RS)-2-[2-(2-methylprop-2-yl)pyrimidin-5-yl]-3-methylbutyrate (Compound XXII) by Method A $^1$H NMR (CDCl$_3$)δ: 0.4 (s, 9H); 0.8, 1.05 (2d, 6H); 1.4 (s, 9H); 2.35 (m, 1H); 3.2 (d, 1H); 5.2 (ABq, 2H); 8.6 (s, 2H).

Infra red (liquid film) : 1745, 1450, 1270, 1145, 865, 850 cm$^{-1}$.

GLC retention time : 8.80 minutes.

(xxii) E,Z-4-(but-2-en-1-yl)-2,3,5,6-tetrafluorobenzyl (RS)-2-[2-(2-methylprop-2-yl)pyrimidin-5-yl]-3-methylbutyrate (Compound XXIII) by Method A 1H NMR (CDCl$_3$)δ: 0.8, 1.05 (2d, 6H); 1.4 (s, 9H); 1.65 (d, 3H); 2.4 (m, 1H); 3.2 (d, 1H); 3.4 (d, 2H); 5.2 (ABq, 2H); 5.5 (m, 2H); 8.6 (s, 2H).

Infra red (liquid film) : 1745, 1490, 1435, 1290, 1145, 1170, 1040, 960 cm$^{-1}$.

(xxiii) 4-(2-Chloroprop-2-en-1-yl)-2,3,5,6-tetrafluorobenzyl (RS)-2-[2-(2-methylprop-2-yl)pyrimidin-5-yl]-3-methylbutyrate (Compound XXIV) by Method A $^1$H NMR (CDCl$_3$)δ: 0.8, 1.05 (2d, 6H); 1.4 (s, 9H); 2.3–2.4 (m, 1H); 3.2 (d, 1H); 3.75 (s, 2H); 5.2 (ABq, 2H); 5.2 (s, 1H); 5.3 (s, 1H); 8.6 (s, 2H).

Infra red (liquid film) : 1740, 1490, 1430, 1280, 1145, 1115, 1050 cm$^{-1}$.

GLC retention time : 9.30 minutes.

(xxiv) 4-Fluoro-3-phenoxybenzyl (RS)-2-[2-(2-methylprop-2-yl)pyrimidin-5-yl]-3-methylbutyrate (Compound XXV) by Method A 1H NMR (CDCl$_3$)δ: 0.8, 1.05 (2d, 6H); 1.4 (s, 9H); 2.3 (m, 1H); 3.2 (d, 1H); 5.0 (ABq, 2H); 6.9–7.4 (m, 8H) 8.65 (s, 2H).

$^{19}$F NMR (CDCl$_3$)δ(relative to CFCl$_3$) : −131.4 (m).

Infra red (liquid film) : 1740, 1590, 1515, 1490, 1430, 1280, 1210, 1150, 1115, 815 cm$^{-1}$.

(xxv) 2-Chloro-6-fluorobenzyl (RS)-2-[2-(2-methylprop-2-yl)pyrimidin-5-yl]-3-methylbutyrate (Compound XXVI) by Method A.

1H NMR (CDCl$_3$)δ: 0.8, 1.05 (2d,6H); 1.4 (s,9H); 2.35 (m,1H); 3.2 (d,1H); 5.25 (ABq,2H); 7.0 (t,1H); 7.2–7.3 (m,2H); 8.6 (s,2H).

Infra red (liquid film) : 1740, 1610, 1585, 1486, 1455, 1430, 1250, 1180, 1160, 990, 780 cm$^{-1}$.

(xxvi) (RS)-1-Cyano-1-(3-benzyl-4-fluorophenyl)-methyl (RS)-2-[2-(2-methylprop-2-yl)pyrimidin-5-yl]-3-methylbutyrate (Compound XXVII) by method A.

$^1$H NMR (CDCl$_3$)δ: 0.75–1.05 (4d,6H); 1.4 (s,9H); 2.35 (m,1H); 3.2 (2d,1H); 4.0 (broad s, 2H); 6.3, 6.35 (2S,1H); 7.0–7.4 (m,8H); 8.6 (2s,2H).

$^{19}$F NMR (CDCl$_3$)δ(relative to CFCl$_3$): −114.289 (s).

Infra red (liquid film) : 1750, 1590, 1550, 1500, 1435, 1245, 1135, 1105, 820, 730, 700 cm$^{-1}$.

(xxvii) 3-(Phenylamino)benzyl (RS)-2-[2-(2-methylprop-2-yl)pyrimidin-5-yl]-3-methylbutyrate (Compound XXVIII) by Method A 1H NMR (CDCl$_3$)δ: 0.8, 1.05 (2d, 6H); 1.4 (s, 9H); 2.35 (m, 1H); 3.2 (d, 1H); 5.1 (ABq, 2H); 5.7 (broad S, 1H); 6.8–7.4 (m, 8H); 8.6 (s, 2H).

Infra red (liquid film) : 3400, 1735, 1595, 1500, 1435, 1180, 1150, 745, 680 cm$^{-1}$.

GLC retention time : 13.24 minutes.

(xxviii) E-4-(2,3-dichloroprop-2-en-1-yl)-2,3,5,6-tetrafluorobenzyl (RS)-2-[2-(2-methylprop-2-yl)pyrimidin-5-yl]-3-methylbutyrate (Compound XXIX) by Method A 1H NMR (CDCl$_3$)δ:0.8, 1.05 (2d, 6H); 1.4 (s, 9H); 2.35 (m, 1H); 3.2 (d, 1H); 3.95 (s, 2H); 5.2 (ABq, 2H); 6.35 (s, 1H); 8.6 (s, 2H)

GLC retention time : 10.26 minutes.

(xxix) Pentafluorobenzyl (RS)-2-[2-(2-methylprop-2-yl)pyrimidin-5-yl]-3-methylbutyrate (Compound XXX) by Method A.

$^1$H NMR (CDCl$_3$)δ: 0.8, 1.05 (2d, 6H); 1.4 (s, 9H); 2.35 (m, 1H); 3.2 (d, 1H); 5.2 (ABq, 2H); 8.6 (s, 2H).

Infra red (liquid film) : 1750, 1530, 1515, 1440, 1140, 950, cm$^{-1}$.

(xxx) 4-(Prop-2-en-1-yl)-2,3,5,6-tetrafluorobenzyl (RS)-2-[4-chloro-2-(2-methylprop-2-yl)pyrimidin-5-yl]-3-methylbutyrate (Compound XXXI) by Method A.

$^1$H NMR (CDCl$_3$) : 0.85, 1.1 (2d, 6H); 1.4 (s, 9H); 2.3 (m, 1H); 3.5 (d, 2H); 3.8 (d, 1H); 5.2 (d, 2H); 5.0 (d, 1H); 5.2 (d, 1H); 5.9 (m, 1H); 8.75 (s, 1H).

Infra red (liquid film) : 1750, 1580, 1490, 1425, 1155 cm$^{-1}$.

(xxxi) 4-(Prop-2-yn-1-yl)-2,3,5,6-tetrafluorobenzyl (RS)-2-[4-chloro-2-(2-methylprop-2-yl)pyrimidin-5-yl]-3-methylbutyrate (Compound XXXII) by Method A.

$^1$H NMR (CDCl$_3$)δ: 0.8, 1.1 (2d, 6H); 1.4 (s, 9H); 2.05 (t, 1H); 2.35 (m, 1H); 3.6 (d, 2H); 3.8 (d, 1H); 5.25 (d, 1H); 8.8 (s, 1H).

Infra red (liquid film) : 1750, 1580, 1495, 1425, 1155, 1050 cm$^{-1}$.

(xxxii) (RS)-1-Cyano-1-(3-phenoxyphenyl)methyl (RS)-2-[4-chloro-2-(2-methylprop-2-yl)pyrimidin-5-yl]-3-methylbuty-rate (Compound XXXIII) by Method A.

$^1$H NMR (CDCl$_3$)δ: 0.8, 0.85, 1.0, 1.1 (4d, 6H); 1.4 (s, 9H); 2.4 (m, 1H); 3.9 (d, 1H); 6.35 (2s, 1H); 7.0–7.4 (m, 9H); 8.75 (s, 1H).

Infra red (liquid film) : 1760, 1710, 1590, 1490, 1425, 1250, 700 cm$^{-1}$.

(xxxiii) (RS)-1-Cyano-(6-phenoxypyrid-2-yl)methyl (RS)-2-[4-chloro-2-(2-methylprop-2-yl)pyrimidin-5-yl]-3-methylbutyrate (Compound XXXIV) by Method A.

$^1$H NMR (CDCl$_3$)δ: 0.8, 0.85, 1.0, 1.15 (4d, 6H); 1.4 (s, 9H); 2.4 (m, 1H); 3.9 (2d, 1H); 6.3 (2s, 1H); 6.95 (t); 7.2 (m); 7.4 (m); 7.75 (m); 8.75 (s,1H).

Infra red (liquid film) : 1745, 1600, 1580, 1450, 1430, 1250 cm$^{-1}$.

(xxxiv) 4-(Prop-2-en-1-yl)-2,3,5,6-tetrafluorobenzyl (RS)-2-[4-fluoro-2-(2-methylprop-2-yl)pyrimidin-5-yl]-3-methylbutyrate (Compound XXXV) by Method B.

$^1$H NMR (CDCl$_3$) δ: 0.8, 1.05 (2d, 6H); 1.4 (s, 9H); 2.4 (m, 1H); 3.45 (d, 2H); 3.6 (d, 1H); 5.2 (ABq, 2H); 5.05 (d, 1H); 5.1 (d, 1H); 5.9 (m, 1H); 8.8 (d, 1H).

Infra red (liquid film) : 1745, 1610, 1490, 1440 cm$^{-1}$.

(xxxv) 4-Methyl-2,3,5,6-tetrafluorobenzyl (RS)-2-[4-fluoro-2-(2-methylprop-2-yl)pyrimidin-5-yl]-3-methylbuty-rate (Compound XXXVI) by Method B.

$^1$H NMR (CDCl$_3$)δ: 0.8, 1.05 (2d, 6H ; 1.4 (s, 9H); 2.3 (m, 1H); 2.3 (t, 3H); 3.6 (d, 1H); 5.2 (d, 2H); 8.8 (d, 1H).

Infra red (liquid film) : 1745, 1610, 1490, 1440, 1290, 1075, 940 cm$^{-1}$.

$^{19}$F NMR (CDCl$_3$)δ: (ppm relative to CFCl$_3$): −66.3 (d). −143.6 (m). −145.2 (m).

(xxxvi) 4-Fluoro-3-phenoxybenzyl (RS)-2-[4-fluoro-2-(2-methylprop-2-yl)pyrimidin-5-yl]-3-methylbutyrate (Compound XXXVII) by Method B.

$^1$H NMR (CDCl$_3$) : 0.8, 1.05 (2d, 6H); 1.4 (s, 9H); 2.2–2.4 (m, 1H); 3.6 (d, 1H); 5.2 (2d, 2H); 6.9–7.4 (m, 8H); 8.6 (d, 1H).

Infra red (liquid film) : 1735, 1610, 1590, 1510, 1490, 1430, 1280, 1210 cm$^{-1}$.

(xxxvii) 4-Methyl-2,3,5,6-tetrafluorobenzyl (RS)-2-[2-(1-methylethyl)pyrimidin-5-yl]-3-methylbutyrate (Compound XXXVIII) by Method B.

$^1$H NMR (CDCl$_3$) : 0.76 (d, 3H); 1.04 (d, 3H); 1.36 (d, 6H); 2.52 (m, 4H); 3.20 (m, 2H); 5.22 (q, 2H); 8.62 (s, 2H).

Infra red (liquid film) : 2980, 2880, 1745, 1590, 1550, 1490, 1440, 1290, 1150, 1075 cm$^{-1}$.

Molecular Ion : 398.

(xxxviii) 4-(Prop-2-en-1-yl)-2,3,5,6-tetrafluorobenzyl (RS)-2-[2-(1-methylethyl)pyrimidin-5-yl]-3-methylbutyrate (Compound XXXIX) by Method B.

$^1$H NMR (CDCl$_3$)δ: 0.76 (d, 3H); 1.04 (d, 3H); 1.36 (d, 6H); 2.34 (m, 1H); 3.20 (m, 2H); 3.48 (d, 2H), 5.18 (m, 4H); 5.90 (m, 1H); 8.62 (s, 2H).

Infra red (liquid film) : 2975, 2880, 1740, 1590, 1550, 1490, 1440, 1150, 1115 cm$^{-1}$.

Molecular Ion : 424.

(xxxix) Pentafluorobenzyl (RS)-2-[2-(1-methylethyl)pyrimidin-5-yl]-3-methylbutyrate (Compound XL) by Method A.

$^1$H NMR (CDCl$_3$)δ: 0.76 (d, 3H); 1.01 (d, 3H); 1.36 (d, 6H); 2.30 (m, 1H); 3.20 (m, 2H); 5.16 (broad, 2H); 8.62 (s, 2H).

Infra red (liquid film) : 2970, 1745, 1520, 1510, 1440, 1310, 1130, 1160, 940 cm$^{-1}$.

Molecular Ion : 402.

(xl) 4-(Prop-2-yn-1-yl)-2,3,5,6-tetrafluorobenzyl (RS)-2-[2-(1-methylethyl)pyrimidin-5-yl]-3-methylbutyrate (Compound XLI) by Method A.

$^1$H NMR (CDCl$_3$)δ: 0.76 (d, 3H); 1.02 (d, 3H); 1.36 (d, 6H); 2.08 (m, 1H); 2.34 (m, 1H); 3.20 (m, 2H); 3.04 (broad, 2H); 5.23 (q, 2H); 8.60 (s, 2H).

Infra red (liquid film) : 3320, 2980, 2880, 1745, 1590, 1550, 1490, 1440, 1285, 1150, 1050, 860 cm$^{-1}$.

Molecular Ion : 422.

(xli) 4-(Prop-2-en-1-yl)-2,3,5,6-tetrafluorobenzyl (RS)-2-[2-(1,1-dimethylprop-1-yl)pyrimidin-5-yl]-3-methylbutyrate (Compound XLII) by Method B.

$^1$H NMR (CDCl$_3$)δ: 0.69 (t, 3H); 0.76 (d, 3H); 1.03 (d, 3H); 1.36 (s, 6H); 1.80 (q, 2H); 2.34 (m, 1H); 3.18 (d, 1H); 3.48 (m, 2H); 5.18 (m, 4H); 5.90 (m, 1H); 8.64 (s, 2H).

Infra red (liquid film) : 2970, 1745, 1640, 1590, 1545, 1485, 1430, 1280, 1140 cm$^{-1}$.

Molecular Ion : 452.

(xlii) 4-(Prop-2-yn-1-yl)-2,3,5,6-tetrafluorobenzyl (RS)-2-[2-(1,1-dimethylprop-1-yl)pyrimidin-5-yl]-3-methylbutyrate (Compound XLIII) by Method A.

$^1$H NMR (CDCl$_3$) δ: 0.68 (t, 3H); 0.75 (d, 3H); 1.02 (d, 3H); 1.36 (s, 6H); 1.80 (q, 2H); 2.06 (m, 1H); 2.34 (m, 1H); 3.18 (d, 1H); 3.62 (broad, 2H); 5.22 (q, 2H); 8.60 (s, 2H).

Infra red (liquid film) : 3320, 2970, 1745, 1590, 1550, 1495, 1430, 1280, 1150, 1050 cm$^{-1}$.

Molecular Ion : 450.

(xliii) 4-(Methoxymethyl)-2,3,5,6-tetrafluorobenzyl (RS)-2-[2-(1,1-dimethylprop-1-yl)pyrimidin-5-yl]-3-methylbutyrate (Compound XLIV) by Method A.

$^1$H NMR (CDCl$_3$)δ: 0.68 (t; 3H); 0.76 (d, 3H); 1.00 (d, 3H); 1.34 (s, 6H); 1.80 (q, 2H); 2.32 (m, 1H); 3.18 (d, 1H); 3.38 (s, 3H); 4.58 (s, 2H); 5.24 (q,2H); 8.64 (s, 2H).

Infra red (liquid film) : 2970, 1745, 1590, 1550, 1495, 1440, 1290, 1150, 1120, 1060.

Molecular Ion : 456.

(xliv) 4-(Prop-2-en-1-yl)-2,3,5,6-tetrafluorobenzyl (RS)-2-[2-cyclopropylpyrimidin-5-yl]-3-methylbutyrate (Compound XLV) by Method B.

$^1$H NMR (CDCl$_3$)δ: 0.76 (d, 3H); 1.06 (m, 7H); 2.28 (m, 2H); 3.14 (d, 1H); 3.48 (m, 2H); 5.16 (m, 4H); 5.88 (m, 1H), 8.50 (s, 2H).

Infra red (liquid film) : 2970, 1740, 1590, 1545, 1485, 1450, 1290, 1150.

Molecular Ion : 422.

(xlv) 4-(Prop-2-yn-1-yl)-2,3,5,6-tetrafluorobenzyl (RS)-2-[2-cyclopropylpyrimidin-5-yl]-3-methylbutyrate (Compound XLVI) by Method B.

$^1$H NMR (CDCl$_3$)δ: 0.78 (d, 3H); 1.04 (m, 7H); 2.06 (m, 1H); 2.24 (m, 2H); 3.16 (d, 1H); 3.66 (m, 2H); 5.20 (broad, 2H); 8.52 (s, 2H).

Infra red (liquid film) : 3320, 2970, 1745, 1590, 1550, 1495, 1455, 1280, 1150, 1050 cm$^{-1}$.

Molecular Ion : 420.

(xlvi) 4-Fluoro-3-benzylbenzyl (RS)-2-[2-cyclopropylpyrimidin-5-yl]-3-methylbutyrate (Compound XLVII) by Method A.

$^1$H NMR (CDCl$_3$)δ: 0.72 (d, 3H); 0.92 (d, 3H); 1.08 (m, 4H); 2.24 (m, 2H); 3.12 (d, 1H); 3.96 (s, 2H); 5.02 (q, 2H); 7.16 (m, 8H); 8.48 (s, 2H).

Infra red (liquid film) : 2970, 1740, 1590, 1550, 1500, 1455, 1250, 1180, 1110 cm$^{-1}$.

Molecular Ion : 418.

(xlvii) 4-(Prop-2-en-1-yl)-2,3,5,6-tetrafluorobenzyl (RS)-2-[2-(1-methylcycloprop-1-yl)pyrimidin-5-yl]-3-methylbutyrate (Compound XLVIII) by Method B.

$^1$H NMR (CDCl$_3$)δ: 0.76 (d, 3H); 0.92 (m, 2H); 1.02 (d, 3H); 1.36 (m, 2H); 1.56 (s, 3H); 2.34 (m, 1H); 3.16 (d, 1H); 3.48 (m, 2H); 5.16 (m, 4H); 5.90 (m, 1H); 8.52 (s, 2H).

Infra red (liquid film) : 2970, 1740, 1590, 1545, 1490, 1470, 1440, 1300, 1280, 1150 cm$^{-1}$.

Molecular Ion : 436.

(xlviii) 4-Fluoro-3-benzylbenzyl (RS)-2-[2-(1-methylcycloprop-1-yl)pyrimidin-5-yl]-3-methylbutyrate (Compound L) by Method A.

$^1$H NMR (CDCl$_3$)δ: 0.72 (d, 3H); 0.92 (m, 5H); 1.36 (m, 2H); 1.66 (s, 3H); 2.30 (m, 1H); 3.14 (d, 1H); 4.96 (s, 2H); 5.00 (q, 2H); 7.15 (m, 8H); 8.52 (s, 2H).

Infra red liquid film) : 2970, 1735, 1590, 1550, 1500, 1470, 1440, 1250, 1150, 1100 cm$^{-1}$.

Molecular Ion : 432.

(xlix) 4-(Prop-2-yn-1-yl)-2,3,5,6-tetrafluorobenzyl (RS)-2-[2-(1-methylcycloprop-1-yl)pyrimidin-5-yl]-3-methylbutyrate (Compound LI) by Method A.

$^1$H NMR (CDCl$_3$)δ: 0.76 (d, 3H); 0.86 (m, 5H); 1.36 (m, 2H); 1.60 (s, 3H); 2.08 (m, 1H), 2.32 (m, 1H); 3.16 (d, 1H); 3.64 (broad, 2H); 5.20 (broad, 2H); 8.56 (s, 2H).

Infra red (liquid film) : 3320, 2970, 1745, 1590, 1550, 1495, 1470, 1440, 1150 cm$^{-1}$.

Molecular Ion : 434.

(l) (RS)-1-Cyano-1-(4-fluoro-3-phenoxyphenyl)methyl (RS)-2-[2-(2-methylprop-2-yl)pyrimidin-5-yl]-3-methylbutyrate (Compound LII) by Method A.

$^1$H NMR (CDCl$_3$)δ: 0.7–1.1 (4d,6H); 1.4 (s,9H); 2.35 (m,1H); 3.25 (2d,1H); 6.25, 6.30 (2s,1H); 6.9–7.4 (m,8H); 8.6 (2s,1H)

Infra red (liquid film) : 2980, 1755, 1595, 1435, 1230, 740 cm$^{-1}$.

EXAMPLE 15

This Example records physical characteristics for the intermediate acids of Method A of Example 14 (see also Example 13).

(i) (RS)-2-[2-(2-methylprop-2-yl)4-chloropyrimidin-5-yl]-3-methylbutyric acid.

$^1$H NMR (CDCl$_3$)δ: 0.85, 1.15 (2d,6H); 1.4 (s,9H); 2.4 (m,1H); 3.85 (d,1H); 9.0 (s,1H).

GLC retention time : 5.21 minutes.

(ii) (RS)-2-[2-(1-methylethyl)pyrimidin-5-yl]-3-methylbutyric acid $^1$H NMR (CDCl$_3$)δ: 0.80 (d,3H); 1.12 (d,3H); 1.33 (d,6H); 2.33 (m,1H); 3.23 (m,2H); 8.20 (broad s, 1H); 8.77 (s,2H).

Infra red (paraffin mull) : 2970, 1720, 1595, 1555, 1475, 1440, 1190, 910 cm$^{-1}$.

(iii) (RS)-2-[2-cyclopropylpyrimidin-5-yl]-3-methylbutyric acid $^1$H NMR (CDCl$_3$)δ: 0.76 (d,3H); 1.07 (m,7H); 2.20 (m,2H); 3.13 (d,1H); 8.53 (s,2H); 9.47 (broad, 1H).

Infra red (liquid film) : 2970, 1720, 1595, 1550, 1460, 1190, 910 cm$^{-1}$.

(iv) (RS)-2-[2-(1-methylcyclopropyl)pyrimidin-5-yl]-3-methylbutyric acid.

$^1$H NMR (CDCl$_3$)δ: 1.05 (m,10H); 1.53 (s,3H); 2.36 (m,1H); 3.18 (d,1H); 8.60 (s,2H); 8.93 (broad s, 1H).

Infra red (liquid film) : 2980, 2570, 1720, 1595, 1550, 1470, 1440, 1160, 735 cm$^{-1}$.

(v) (RS)-2-[2-(1,1-dimethylprop-1-yl)pyrimidin-5-yl]-3-methylbutyric acid $^1$H NMR (CDCl$_3$)δ: 0.70 (t,3H); 0.78 (d,3H); 1.10 (d,3H); 1.37 (s,6H); 1.87 (m,2H); 2.34 (m,1H); 3.23 (d,1,1H); 7.30 (broad, 1H); 8.73 (s,2H).

Infra red (liquid film) : 2970, 1715, 1595, 1550, 1465, 1435, 1190 cm$^{-1}$.

EXAMPLE 16

This Example illustrates the preparation of 2,2-dimethylbutyronitrile.

A solution of n-butyronitrile (5 g) in dry tetrahydrofuran (50 cm$^3$) was cooled to −78° C. by external cooling. To this solution was gradually added a solution of lithium hexamethylsilazide (220 cm$^3$ of a 1 molar solution in tetrahydrofuran), the temperature of the reaction mixture being maintained at approximately −70° C.; the solution was then stirred at −70° C. for 1.25 hours, and methyl iodide (31 g) was then added gradually. The reaction mixture was allowed to warm to the ambient temperature (ca. 20° C.), and stood for 18 hours. The reaction mixture was then cautiously added to water and the product extracted with diethyl ether. The combined organic layers were dried over anhydrous magnesium sulphate and the solvent evaporated under reduced pressure. The residual oil was purified by fractional distillation at atmospheric pressure to give 2,2-dimethylbutyronitrile (1.1 g).

Boiling point: 128°–129° C.

$^1$H NMR (CDCl$_3$)δ: 0.98 (t, 3H); 1.24 (s, 6H); 1.47 (q, 2H).

Infra red (liquid film) : 2990, 2950, 2790, 2240, 1470 1390, 1370, 1015 cm$^{-1}$.

EXAMPLE 17

This Example illustrates the stages in the preparation of 1-methylcyclopropanecarbonitrile.

(i) Preparation of 1-methylcyclopropanecarboxylic acid chloride.

Oxalyl chloride (59.7 g) was added in portions to a stirred solution of 1-methylcyclopropanecarboxylic acid (40 g - commercially available from Aldrich Chemical Company Ltd) in chloroform (300 cm$^3$). The reaction mixture was then heated at the reflux temperature for 3 hours. After this time, the volatile components were removed by distillation at atmospheric pressure to leave a pale yellow liquid (49 g) which was shown by gas liquid chromatography to contain a small amount of unreacted oxalyl chloride. The product was used without further purification.

Infra red (liquid film) δ: 2980, 1850, 1780, 1430, 1300, 1285, 1055, 1080, 930 cm$^{-1}$.

(ii) Preparation of 1-methylcyclopropanecarboxamide.

A solution of 1-methylcyclopropanecarboxylic acid chloride (49 g) in chloroform (300 cm$^3$) was added gradually to a concentrated aqueous solution of ammonia (300 cm$^3$), previously cooled to 0° C. by external cooling. The reaction mixture warmed spontaneously to 20° C. and a white solid precipitate was formed; the precipitate was redissolved by further addition of chloroform. The organic layer was separated, dried over anhydrous magnesium sulphate and the solvent evaporated under reduced pressure. The residual solid was recrystallised from a mixture of chloroform and n-hexane to give 1-methylcyclopropanecarboxamide (17.6g) as colourless crystals.

Melting point: 148° C.

Infra red (paraffin mull): 3390, 3200, 1660, 1615, 1405, 1245, 1110, 880 cm$^{-1}$.

(iii) Preparation of 1-methylcyclopropanecarbonitrile.

A mixture of 1-methylcyclopropanecarboxamide (7.0 g) and excess phosphorus pentoxide was heated at 200° C. 1-Methylcyclopropanecarbonitrile was continuously distilled from the reaction flask during heating and was collected by condensation (2.3 g).

Boiling point: 126° C.

Infra red (liquid film): 2980, 2950, 2250, 1465, 1430, 1035, 955, 895cm$^{-1}$.

$^1$H NMR (CDCl$_3$)δ:0.76 (m, 2H); 1.24 (m, 2H); 1.40 (s, 3H).

EXAMPLE 18

This Example illustrates the preparation of 4-(prop-2-yn-1-yl)-2,3,5,6-tetrafluorobenzyl alcohol, an intermediate in the preparation of Compound XII.

(a) A stirred mixture of pentafluorobenzaldehyde (17.7 g), anhydrous lithium bromide (8.9 g) and N-methylpyrrolidone (50 cm$^3$) was heated at 160° C. under a nitrogen atmosphere for 2 hours, after which it was cooled and poured into water. The solid precipitate was collected by filtration, washed on the filter with water and dried in a dessicator over phosphorus pentoxide. After trituration with diethyl ether the residual solid was collected to yield 4-bromopentafluorobenzaldehyde (8.4 g), m.p. 105°-108° C.

Infra red (paraffin mull):1700 cm$^{-1}$.

(b) Sodium borohydride (1.0 g) was added portionwise over a period of 30 minutes to a stirred solution of 4-bromo-2,3,5,6-tetrafluorobenzaldehyde (8.2 g) in methanol (80 cm$^3$) whilst the temperature was maintained within the range from −5° C. to +5° C., after which the mixture was stirred for 2 hours at the ambient temperature (ca. 18° C.). The mixture was poured into water and the precipitated white solid collected by filtration, washed with water and air dried to yield 4-bromo-2,3,5,6-tetrafluorobenzyl alcohol (7.5 g), m.p. 60°-62° C.

Infra red (paraffin mull):3400(b), 1500(b) cm$^{-1}$.

(c) Dihydropyran (3.0 g) and concentrated hydrochloric acid (0.3 cm$^3$) were added successively to a stirred solution of 4-bromo-2,3,5,6-tetrahydrobenzyl alcohol (8.4 g) in dry diethyl ether (50 cm$^3$) and the mixture stirred for a further 15 minutes after which the more volatile components were removed by evaporation under reduced pressure. The residual oil was confirmed by spectroscopic analysis as being 2-(4-bromo-2,3,5,6-tetrafluorobenzyloxy)tetrahydropyran (9.5 g) of ca. 95% purity.

$^1$H NMR (CDCl$_3$)δ:4.6 (m, 3H); 3.9 (m, 2H); 1.6 (m, 6H).

(d) n-Butyllithium (2.3 cm$^3$ of a 2.5 M solution in -hexane) was added dropwise to a solution of 2-(4-bromo-2,3,5,6-tetrafluorobenzyloxy)tetrahydropyran (1.7 g) in dry tetrahydrofuran (50 cm$^3$) maintained at a temperature of −70° C. under a nitrogen atmosphere, and the resulting mixture stirred for a further 2 hours. Copper (I) bromide-dimethylsulphide complex (1.1 g) was added to the mixture and after stirring for a further 2 hours, propargyl chloride (0.4 g) was added dropwise to the clear brownish-yellow solution. The mixture was maintained at −70° C. for 1 hour and then allowed to warm to the ambient temperature over a period of 4 hours. The mixture was partitioned between diethyl ether and aqueous saturated ammonium chloride solution, and the ethereal phase separated, washed with water and dried over anhydrous magnesium sulphate. Removal of the solvent by evaporation under reduced pressure yielded a residual oil (1.4 g) consisting of ca. 60% of the desired product together with ca. 20% 2-(2,3,5,6-tetrafluorobenzyloxy)tetrahydrofuran, and ca. 20% other unidentified materials. Purification and separation was effected by means of hplc (Gilson) using a silica column eluted with a mixture of n-hexane (9 parts by volume) and diethyl ether (1 part by volume) to yield pure 2-[4-(prop-2-yn-1-yl)-2,3,5,6-tetrafluorobenzyloxy]tetrahydropyran (0.8 g).

$^1$H NMR (CDCl$_3$)δ:4.6 (m, 3H); 3.9 (m, 2H); 3.6 (d, 2H); 2.0 (t, 1H); 1.6 (m, 6H).

Infra red (liquid film):3300, 2700 cm$^{-1}$.

(e) A mixture of 2-[4-(prop-2-yn-1-yl)-2,3,5,6-tetrafluorobenzyloxy]tetrahydropyran (0.8 g), dilute hydrochloric acid (2N, 5 cm$^3$) and methanol (30 cm$^3$) was stirred together at the ambient temperature for 2 hours, after which the more volatile portion was removed by evaporation under reduced pressure. The residue was extracted with diethyl ether, the extracts combined, washed with water, and dried over anhydrous magnesium sulphate. Removal of the solvent by evaporation under reduced pressure yielded an oil which crystallised on standing to give 4-(prop-2-yn-1-yl)-2,3,5,6-tetrafluorobenzyl alcohol (0.5 g), m.p. 51°-52° C., after recrystallisation from petroleum ether (boiling range 60°-80° C.).

$^1$H NMR (CDCl$_3$)δ:4.8 (s, 2H); 3.6 (m, 2H); 2.3 (broad s, 1H); 1.0 (t, 1H).

Infra red (paraffin mull): 3400 cm$^{-1}$.

EXAMPLE 19

This Example illustrates the stages in the preparation of 3-benzyl-4-fluorobenzyl alcohol, an intermediate in the preparation of Compounds XVIII, XLVII and L.

Stage 1: Preparation of 3-bromo-4-fluorobenzaldehyde.

A solution of 4-fluorobenzaldehyde (49.6 g) in dry dichloromethane (200 cm$^3$) was added to a cooled (0° C.) suspension of powdered aluminium trichloride (90.4 g) in dry dichloromethane (100 cm$^3$). Bromine (70.4 g) was added, and the mixture heated at the reflux temperature of 16 hours. After cooling, the reaction mixture was carefully poured onto ice and extracted with dichloromethane. The combined organic layers were washed with saturated sodium metabisulphite solution, water and brine, then dried over anhydrous magnesium sulphate. Evaporation of the solvent under reduced pressure gave a dark red oil, which was purified by distillation under reduced pressure, using a 4" Vigreux column to give 3-bromo-4-fluorobenzaldehyde (45.7 g) as an oil, boiling point 85°–108° C. at 8 mmHg.

Stage 2: Preparation of 2-(3-bromo-4-fluorophenyl)-1,3-dioxolane.

A mixture of 3-bromo-4-fluorobenzaldehyde (45.7 g), ethylene glycol (27.39 g), p-toluenesulphonic acid (0.225 g) and dry toluene (110 cm$^3$) was heated at the reflux temperature under a Dean and Stark trap. After 4.5 hours, approximately 12 cm$^3$ of water had collected in the trap, and analysis of the reaction mixture by gas liquid chromatography indicated that no starting aldehyde was present. The mixture was washed with sodium bicarbonate solution and brine, and dried over anhydrous magnesium sulphate. Evaporation of the solvent under reduced pressure gave a yellow oil, which was purified by distillation under reduced pressure to give 2-(3-bromo-4-fluorophenyl)-1,3-dioxolane (43.56 g), boiling point 68°–106° C. at 0.04 mmHg.

90 MHz $^1$H NMR (CDCl$_3$)δ(ppm):4.1 (4H,m); 5.8 (1H,s); 7.0–7.7 (3H,m).

Stage 3: Preparation of 2-(3-benzyl-4-fluorophenyl)-1,3-dioxolane.

This compound was prepared by a method analogous to that reported by Minato et al in Tetrahedron Letters, 21, 845, 1980.

Benzyl bromide (2.77 g) was added in one addition to a suspension of activated zinc powder (2.1 g) in dry tetrahydrofuran (20 cm$^3$) under an atmosphere of nitrogen. The reaction mixture was sonicated for 2 hours, allowed to stand for 30 minutes and carefully filtered under an atmosphere of nitrogen. The filtered solution was then added to a mixture of 2-(3-bromo-4-fluorophenyl)-1,3-dioxolane (1 g) and palladium (0) tetrakis triphenylphosphine (0.05 g) in dry tetrahydrofuran (10 cm$^3$) under an atmosphere of nitrogen. The stirred mixture was heated at the reflux temperature for 48 hours, at which time analysis by gas liquid chromatography showed no trace of starting material. The reaction mixture was cooled and poured into diethyl ether. The organic layer was separated, and washed with ammonium chloride solution, water and brine, then dried over anhydrous magnesium sulphate. Evaporation of the solvent under reduced pressure gave a yellow oil which was purified by column chromatography on a silica gel support, using petroleum ether (boiling range 40°–60° C.) containing diethyl ether (progressively increased from 10% to 20% by volume) as eluent to give 2-(3-benzyl-4-fluorophenyl)-1,3-dioxolane (0.7 g). The product was used without further purification.

60 HMz $^1$H NMR (CDCl$_3$ δ(ppm):4.0 (6H,m); 5.7 (1H,s); 6.8–7.5 (8H,m).

Stage 4: Preparation of 3-benzyl-4-fluorobenzaldehyde.

A mixture of 2-(3-benzyl-4-fluorophenyl)-1,3-dioxolane (0.7 g) acetone (10 cm$^3$), water (1 cm$^3$) and concentrated sulphuric acid (5 drops) was stirred for 16 hours. The reaction mixture was poured into diethyl ether and the organic layer washed with sodium bicarbonate solution, water and brine, then dried over anhydrous magnesium sulphate. Evaporation of the solvents under reduced pressure gave 3-benzyl-4-fluorobenzaldehdye (0.59 g), which was used without further purification.

$^1$H NMR (CDCl$_3$)δ(ppm) :4.10 (2H,s); 7.20 (6H,m); 7.75 (2H,m); 9.90 (1H,s).

IR (liquid film):1700 cm$^{-1}$ (C=O).

Stage 5: Preparation of 3-benzyl-4-fluorobenzyl alcohol.

A solution of 3-benzyl-4-fluorobenzaldehyde (5 g) in methanol (75 cm$^3$) was cooled to 0° C. Sodium borohydride (1.34 g) was added in portions, and the mixture stirred for 1 hour. The reaction mixture was then poured cautiously into a mixture of water and diethyl ether, and the organic layer was separated, washed with water and brine, and dried over anhydrous magnesium sulphate. Evaporation of the solvents under reduced pressure gave a pale yellow oil which was purified by distillation in a kugelrohr apparatus to give 3-benzyl-4-fluorobenzyl alcohol (4.0 g).

Boiling point:120° C. at 0.02 mmHg.

$^1$H NMR (CDCl$_3$)δ(ppm):1.7 (1H,broad s); 4.0 (2H,s); 4.6 (2H,s); 7.0–7.3 (8H,m).

IR (liquid film):3600–3100 cm$^{-1}$ (OH).

EXAMPLE 20

This Example illustrates the preparation of methyl 2-methoxy-4-methoxymethyl-3,5,6-trifluorobenzoate as a by-product in the preparation of methyl 4-methoxymethyl-2,3,5,6-tetrafluorobenzoate and its conversion to 2-methoxy-4-methoxymethyl-3,5,6-trifluorobenzyl alcohol, an intermediate in the preparation of compound XVI.

(i) Methyl 4-bromomethyl-2,3,5,6-tetrafluorobenzoate (10 g, prepared as described in U.S. Pat. No. 4,370,346) was dissolved in dry methanol (10 cm$^3$) and the solution added dropwise to a solution of sodium methoxide in dry methanol obtained by dissolving sodium metal (1.5 g) in dry methanol (20 cm$^3$) at the ambient temperature (ca. 22° C.). When the addition was completed the excess methanol was removed by evaporation under reduced pressure. Water was added and the mixture acidified with dilute hydrochloric acid and extracted with ethyl acetate. After drying the extracts over anhydrous magnesium sulphate and removing the solvent by evaporation under reduced pressure the residue, which partially solidified, was triturated with petroleum ether (boiling range 40°–60° C.) and the solid separated by filtration. (The solid (4.0 g) was shown by nmr and infra red analysis to be 4-methoxymethyl-2,3,5,6-tetrafluorobenzoic acid, mp. 92°–95° C. after recrystallisation from a petroleum ether/chloroform mixture). The filtrate was washed with dilute sodium hydroxide solution and with water, separated, dried over anhydrous magnesium sulphate and concentrated by evaporation under reduced pressure to give a residue (1.4 g) which was purified by h.p.l.c. (Gilson) using a silica column and as eluent a mixture of petroleum ether (boiling range 40°–60° C. 3 parts by volume) and diethyl ether (one part by volume) to yield a slower running product (600 mg) and a faster running product (650 mg). These were shown by nmr spectroscopy to be methyl 4-methoxymethyl-2,3,5,6-tetrafluorobenzoate and methyl 2-methoxy-4-methoxymethyl-3,5,6-trifluorobenzoate respectively.

(ii) A mixture of methyl 2-methoxy-4-methoxymethyl-3,5,6-trifluorobenzoate (600 mg), lithium bromohydride (50 mg) and dry diethyl ether (20 cm$^3$) was stirred for two hours and kept at the ambient temperature for a further sixteen hours after which the desired product was isolated by the procedure illustrated in Example 4. 2-Methoxy-4-methoxymethyl-3,5,6-trifluorobenzyl alcohol (370 mg) was identified by nmr and infra red spectroscopy.

EXAMPLE 21

This Example illustrates the synthesis of (RS)-α-cyano-3-benzyl-4-fluorobenzyl alcohol, an intermediate in the preparation of Compound XXVII.

A solution of potassium cyanide (0.26 g) in water (2 cm$^3$) was added portionwise to a suspension of 3-benzyl-4-fluorobenzaldehyde (0.5 g) in glacial acid (10 cm$^3$) whilst the temperature was maintained at 0° C. After 30 minutes, the reaction mixture was allowed to warm to the ambient temperature (ca. 25° C.), and allowed to stand for a period of 16 hours. A further portion of glacial acetic acid (5 cm$^3$) was added and stirring continued for 8 hours at the ambient temperature. After standing for sixteen hours, a further portion of potassium cyanide (0.26 g) in water (1 cm$^3$) was added, and after the reaction mixture had been allowed to stand for a period of 7 days, it was diluted with water, and extracted with diethyl ether. The ethereal layer was washed sequentially with aqueous sodium bicarbonate, and brine, dried, and the solvent evaporated under reduced pressure. The residue was subjected to column chromatography on silica gel using hexane containing diethyl ether (40% by volume) as eluent to give firstly recovered 3-benzyl-4-fluorobenzaldehyde (0.2 g), and secondly α-cyano-3-benzyl-4-fluorobenzyl alcohol (0.24 g) as a white solid.

90 MHz $^1$H NMR (CDCl$_3$)δ:4.05 (2s,2H); 5.45 (s,1H); 7.1–7.4 (m,7H); 7.9–8.0 (m,1H).

EXAMPLE 22

This Example illustrates the stages in the preparation of Z-4-(3-chloroprop-2-en-1-yl)-2,3,5,6-tetrafluorobenzyl alcohol, an intermediate in the preparation of Compound XIV.

(i) Preparation of Z-1-chloro-3-iodoprop-1-ene. A solution of Z-1,3-dichloropropene (4.05 g) and Potassium iodide (6.0 g) in dry acetone (75 cm$^3$) was heated to the reflux temperature for a period of two hours. After cooling to the ambient temperature (ca. 25° C.), the reaction mixture was poured into aqueous sodium thiosulphate solution, and then extracted with diethyl ether. The organic layer was washed with water, and brine, dried, and the solvent evaporated under reduced pressure to give Z-1-chloro-3-iodoprop-1-ene as an orange oil (2.4 g). This material was immediately carried through to the next stage.

GLC retention time:1.04 minutes.

(ii) Preparation of 2-[Z-4-(3-chloroprop-2-en-1-yl)-2,3,5,6-tetrafluorobenzyloxy]tetrahydropyran.

n-Butyl lithium (2.5 M in hexane, 3 cm$^3$) was added portionwise to a solution of 2-[4-bromo-2,3,5,6-tetrafluorobenzyloxy]-tetrahydropyran (1.7 g) in dry tetrahydrofuran (10 cm$^3$) under an atmosphere of dry nitrogen, whilst the reaction temperature was maintained at −70° C. After 30 minutes, copper (I) bromide - dimethyl sulphide complex (1.54 g) was added in one portion and the reaction temperature allowed to warm to 0° C., for a period of 15 minutes. After cooling to −70° C., a solution of Z-1-chloro-3-iodoprop-1-ene (2.03 g) in dry tetrahydrofuran (3 cm$^3$) was added portionwise, and the reaction mixture stirred for a further hour at −70° C. After warming to the ambient temperature, (ca. 25° C.), aqueous ammonium chloride was added to the reaction mixture, which was then extracted with ethyl acetate. After drying, the solvent was evaporated under reduced pressure to give an orange oil. The residue was then subjected to medium pressure column chromatography on a silica gel column using a Gilson apparatus, eluting with petroleum ether (boiling range 40°–60° C.) containing diethyl ether (5% by volume) to give 2-[4-(3-chloroprop-2-en-1-yl)-2,3,5,6-tetrafluorobenzyloxy]-tetrahydropyran, as a mixture consisting predominantly of the Z isomer.

$^1$H NMR (CDCl$_3$)δ:1.5–1.8 (m,6H); 3.5 (m,1H); 3.65 (d,2H); 3.90 (m,1H); 4.60 (d,1H); 4.8 (m,2H); 5.8 (q,1H); 6.15 (m,1H).

GLC retention time:5.98 minutes.

(iii) Preparation of Z-4-(3-chloroprop-2-en-1-yl)-2,3,5,6-tetrafluorobenzyl alcohol.

The tetrahydropyranyl ether prepared in stage (ii) was dissolved in methanol (30 cm$^3$), and to the stirred solution was added a catalytic amount of concentrated hydrochloric acid. After stirring for two hours, the reaction mixture was diluted with water, and extracted with ethyl acetate. The organic layer was washed and dried, and the solvent evaporated under reduced pressure to give Z-4-(3-chloroprop-2-en-1-yl)-2,3,5,6-tetrafluorobenzyl alcohol (0.6 g) as a colourless oil, which solidified on standing.

$^1$H NMR (CDCl$_3$)δ:3.65 (d,2H); 4.8 (s,2H); 5.85 (q,1H); 6.2 (m,1H).

Infra red (liquid film):3640, 1490, 1300, 1250 and 1040 cm$^{-1}$.

GLC retention time:3.08 minutes.

EXAMPLE 23

This Example illustrates the stages in the preparation of 4-(2-chloroprop-2-en-1-yl)-2,3,5,6-tetrafluorobenzyl alcohol, an intermediate in the preparation of compound XXIV.

(i) Preparation of 2-[4-(2-chloroprop-2-en-1-yl)-2,3,5,6-tetrafluorobenzyloxy]tetrahydropyran. n-Butyl lithium (2.5 M in hexane, 2.3 cm$^3$) was added portionwise to a solution of 2-[4-bromo-2,3,5,6-tetrafluorobenzyloxy]tetrahydropyran (1.7 g) in dry tetrahydrofuran (10 cm$^3$) under an atmosphere of dry nitrogen, whilst the reaction temperature was maintained between −30° and −20° C. After 15 minutes, copper (I) bromide-dimethyl sulphide complex (1.2 g) was added in one portion and the reaction temperature was maintained at −10° C. for 1 hour, after which time 1,2-dichloroprop-2-ene 1 cm$^3$) was added, the reaction temperature then being allowed to warm to +15° C. After 3 hours, water followed by saturated aqueous ammonium chloride was added to the reaction mixture, which was then extracted into diethyl ether. The organic layer was then washed with water and brine, dried, and the solvent evaporated under reduced pressure. The residue was then subjected to medium pressure column chromatography on a silica gel column using a Gilson apparatus, eluting with petroleum ether (boiling range 30°–40° C.) containing diethyl ether (10% by volume) to give 2-[4-(2-chloroprop-2-en-1-yl)-2,3,5,6-tetrafluorobenzyloxy]tetrahydropyran (1.5 g).

90 MHz $^1$H NMR (CDCl$_3$)δ:1.4–1.9 (m,6H); 3.4–4.0 (m,2H); 3.8 (s,2H); 4.45–5.0 (m,3H); 5.2 (m,2H).

Infra red (liquid film):2950, 1630, 1470, 1260, and 1050 cm$^{-1}$.

GLC retention time:6.26 minutes.

(ii) Preparation of 4-(2-chloroprop-2-en-1-yl)-2,3,5,6-tetrafluorobenzyl alcohol.

The tetrahydropyranyl ether prepared in stage (ii) (0.2 g), was dissolved in methanol (6 cm$^3$), and to the stirred solution was added concentrated hydrochloric acid (several drops). After stirring for 6 hours, and standing for a further 14 hours, the reaction mixture was poured into water, and extracted with ethyl acetate. The organic layer was washed with water, and brine, dried, and the solvent evaporated under reduced pressure to give 4-(2-chloroprop-2-en-1-yl)-2,3,5,6-tetrafluorobenzyl alcohol as an orange oil (0.15 g).

90 MHz $^1$H NMR (CDCl$_3$)δ:3.8 (broad s, 2H); 4.8 (broad s, 2H); 5.2, 5.25 (2s, 2H).

GLC retention time:2.45 minutes.

EXAMPLE 24

This Example illustrates the stages in the preparation of 4-trimethylsilyl-2,3,5,6-tetrafluorobenzyl alcohol, an intermediate in the preparation of compound XXII.

(i) Preparation of 2-[4-trimethylsilyl-2,3,5,6-tetrafluorobenzyloxy]-tetrahydropyran.

A solution of n-butyl lithium (1.5 M in hexane, 2.9 cm$^3$) was added portionwise to a solution of 4-bromo-2,3,5,6-tetrafluorobenzyloxy]-tetrahydropyran (1.5 g) in dry tetrahydrofuran (43 cm$^3$) under an atmosphere of dry nitrogen, whilst the reaction temperature was maintained at −70° C. As the last portion of base was added, an intense purple colour developed. Chlorotrimethylsilane (1.6 cm$^3$, dried over alumina) was added portionwise, leading immediately to a dissipation of the purple colouration. The reaction mixture was then poured into water, and extracted into ethyl acetate. The organic layer was washed with water and brine, dried, and the solvent evaporated under reduced pressure to give 2-[4-trimethylsilyl-2,3,5,6-tetrafluorobenzyloxy]-tetrahydropyran. This crude material (94% pure by Gas Chromatography) was carried immediately to the next stage, without further purification.

90 MHz $^1$H NMR (CDCl$_3$)δ:0.5 (s,9H); 1.4–2.1 (m,6H); 3.4–4.4 (m,2H); 4.5–5.2 (m,3H).

GLC retention time:5.07 minutes.

(ii) Preparation of 4-trimethylsilyl-2,3,5,6-tetrafluorobenzyl alcohol.

The crude tetrahydropyranyl ether prepared in Stage (i) was dissolved in methanol (20 cm$^3$), and to the stirred solution was added concentrated hydrochloric acid (3 drops). After stirring for 16 hours at the ambient temperature (ca. 25° C.), the reaction mixture was poured into ethyl acetate, washed with water and brine, and dried. Evaporation of the solvent under reduced pressure gave a yellow oil which was subjected to column chromatography on silica gel using petroleum ether (boiling range 40°–60° C.) containing diethyl ether (10% gradually increased to 40% by volume) as eluent to give 4-trimethylsilyl-2,3,5,6-tetrafluorobenzyl alcohol (0.79 g).

90 MHz $^1$H NMR (CDCl$_3$)δ:0.4 (s,9H); 1.9 (t,1H); 4.8 (m,2H).

$^{19}$F NMR (CDCl$_3$) ppm (relative to CFCl$_3$)δ: −128.75 (dd); −145.90 (dd).

Infra red (liquid film):3640, 1450, 1275, and 850 cm$^{-1}$.

GLC retention time:2.24 minutes.

EXAMPLE 25

This Example illustrates the preparation of Z-4-(2,3-dichloroprop-2-en-1-yl)-2,3,5,6-tetrafluorobenzyl alcohol, an intermediate in the preparation of Compound XXIX.

A solution of 4-(prop-2-yn-1-yl)-2,3,5,6-tetrafluorobenzyl alcohol (0.1 g) copper (II) chloride (1.3 g), and lithium chloride (0.62 g) in dry acetonitrile (23 cm$^3$) was heated at the reflux temperature for 40 hours. The resulting dark solution was poured into dilute hydrochloric acid, and extracted into ethyl acetate. The organic phase was washed with more dilute hydrochloride acid, dried, and the solvent evaporated under reduced pressure to give Z-4-(2,3-dichloroprop-2-en-1-yl)-2,3,5,6-tetrafluorobenzyl alcohol (0.1 g) as an orange oil.

$^1$H NMR (CDCl$_3$)δ:1.95 (broad s, 1H); 3.95 (s,2H); 4.8 (s,2H); and 6.35 (s,1H).

Infra red (liquid film): 3400, 1490, 1285, 1055 and 820 cm$^{-1}$.

GLC retention time 3.82 minutes.

EXAMPLE 27

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

In the case of the species *Musca domestica* (housefly), additional tests to determine the knockdown effect of the compounds were performed. Details are given in Table III.

The results of the tests are given in Table IV for each of the Products, at the rate in parts per million given in the second column as a grading of mortality designated as A, B or C wherein A indicates 80–100% mortality or knockdown, B indicates 50–79% mortality or knockdown and C indicates less than 50% mortality or knockdown.

In Table IV the pest organism used is designated by a letter code and the pests species, the support medium or food, and the type and duration of test is given in Table III.

TABLE III

| CODE LETTERS (Table IV) | TEST SPECIES | SUPPORT MEDIUM/FOOD | TYPE OF TEST | DURATION (days) |
|---|---|---|---|---|
| TUa | *Tetranychus urticae* (spider mites - adult) | French bean leaf | Contact | 3 |
| TUe | *Tetranychus urticae* (spider mites - ova) | French bean leaf | Contact | 3 |
| MP | *Myzus persicae* (aphids) | Chinese Cabbage leaf | Contact | 3 |
| NL | *Nilaparvata lugens* | Rice plant | Contact | 3 |

TABLE III-continued

| CODE LETTERS (Table IV) | TEST SPECIES | SUPPORT MEDIUM/FOOD | TYPE OF TEST | DURATION (days) |
|---|---|---|---|---|
| | (brown plant hopper - nymphs) | | | |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| MD/KD | *Musca domestica* (houseflies - adults) | Cotton/wool sugar | Knockdown | 4 hours |
| SP | *Spodoptera exigua* (lesser army worm - larvae) | Cotton leaf | Residual | 3 |

"Contact" test indicates that both pests and medium were treated and "residual" indicates that the medium was treated before infestation with the pests.

TABLE IV

| Compound No. | Rate (ppm) | $TU_A$ | $TU_E$ | MP | NL | MD/KD | MD | BG | HV | SP | DB |
|---|---|---|---|---|---|---|---|---|---|---|---|
| I | 500 | A | C | A | C | — | B | A | A | — | C |
| II | 500 | A | C | A | C | — | A | C | A | — | B |
| III | 500 | A | A | A | C | A | A | C | A | — | C |
| IV | 500 | A | A | A | C | A | A | C | A | — | C |
| V | 500 | A | A | A | C | A | A | B | A | — | C |
| VI | 500 | A | A | B | C | C | C | C | C | — | C |
| VII | 500 | A | A | A | B | A | A | B | B | — | C |
| VIII | 500 | A | C | B | C | B | C | C | B | — | C |
| IX | 500 | A | A | A | C | A | B | C | A | — | C |
| X | 500 | A | A | A | C. | A | A | C | A | — | C |
| XI | 500 | A | A | A | C | A | A | B | A | — | A |
| XII | 500 | A | A | A | C | A | A | B | A | — | A |
| XIII | 500 | A | A | A | B | A | A | B | — | — | A |
| XIV | 500 | A | A | A | B | A | B | C | — | — | B |
| XV | 500 | A | A | A | A | A | A | C | A | A | C |
| XVI | 500 | A | A | A | A | A | A | C | A | A | A |
| XVII | 500 | A | A | C | C | C | C | C | C | C | C |
| XVIII | 500 | A | A | A | B | A | A | C | A | A | C |
| XIX | 500 | A | A | C | C | A | A | C | C | A | C |
| XX | 500 | A | A | A | A | C | C | C | A | A | C |
| XXI | 500 | A | A | A | C | B | A | C | A | A | A |
| XXII | 500 | A | A | B | C | A | A | C | A | A | A |
| XXIII | 500 | A | C | A | A | C | C | C | A | C | A |
| XXIV | 500 | A | A | A | C | A | C | C | C | C | C |
| XXV | 500 | A | A | A | C | C | C | C | A | A | A |
| XXVI | 500 | A | A | C | C | C | C | B | B | A | A |
| XXVII | 500 | A | C | A | B | A | A | C | A | B | C |
| XXVIII | 500 | A | C | C | A | A | C | C | C | C | C |
| XXIX | 500 | A | A | A | C | A | A | C | C | B | B |
| XXX | 500 | A | A | A | C | A | A | — | A | A | A |
| XXXI | 500 | A | A | A | C | A | C | C | B | A | C |
| XXXII | 500 | A | A | A | A | A | A | C | B | A | A |
| XXXIII | 500 | A | C | A | C | A | A | C | C | A | B |
| XXXIV | 500 | B | C | C | C | A | C | C | C | C | C |
| XXXV | 500 | A | A | A | A | A | A | B | A | A | A |
| XXXVI | 500 | A | C | C | C | B | B | C | C | A | C |
| XXXVII | 250 | C | A | A | B | C | C | C | A | A | C |
| XXXVIII | 500 | A | C | A | C | A | A | A | A | A | A |
| XXXIX | 500 | A | A | A | A | A | A | B | A | A | A |
| XL | 500 | A | C | A | B | A | A | A | A | A | A |
| XLI | 500 | A | B | A | A | A | A | A | B | A | A |
| XLII | 500 | A | A | A | A | A | A | C | B | A | C |
| XLIII | 500 | A | A | A | A | A | A | C | B | A | A |
| XLIV | 500 | A | A | A | C | A | B | C | A | B | C |
| XLV | 500 | A | A | A | A | A | A | B | C | A | B |
| XLVI | 100 | A | C | A | C | C | A | B | C | A | A |
| XLVII | 500 | C | C | A | C | C | A | C | A | A | C |
| XLVIII | 500 | A | A | A | A | A | A | A | C | A | A |
| XLIX | 500 | B | B | A | C | A | A | C | A | A | A |
| L | 500 | C | A | B | C | C | A | C | A | A | C |
| LI | 100 | A | A | A | C | C | A | C | B | A | A |
| LII | 500 | A | A | A | A | A | A | C | A | A | A |

We claim:

1. A compound of the formula:

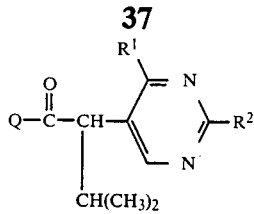

wherein R¹ represents hydrogen or halogen, R² represents an α-branched alkyl or a cycloalkyl group containing from 3 to 6 carbon atoms, which is optionally substituted by methyl Q represents hydroxy, halo, alkoxy of up to 6 carbon atoms or a group of formula:

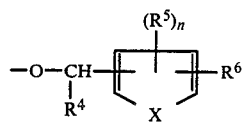

wherein X is oxygen, sulphur, vinylene or a group of formula -CR⁵=Y— where Y is nitrogen or CR⁵, R⁴ is hydrogen, methyl, cyano or ethynyl, each R⁵ is selected from hydrogen, halogen, alkoxy of up to 4 carbon atoms, alkyl of up to 4 carbon atoms optionally substituted with halogen, n has a value selected from 0, 1 or 2, and R⁶ is hydrogen, halogen, alkyl of up to 4 carbon atoms, alkoxy of up to 4 carbon atoms, alkenyl of up to 6 carbon atoms, haloalkenyl of up to 6 carbon atoms, alkynyl of up to 4 carbon atoms, alkoxyalkyl of up to a total of 4 carbon atoms, phenyl, phenoxy or benzyl or phenyl phenony or benzyl substituted with halogen or alkyl.

2. A compound according to claim 2 wherein Q represents an alkoxy of up to 6 carbon atoms, R¹ is hydrogen, chloro or fluoro, and R² is prop-2-yl, but-2-yl, pent-2-yl, pent-3-yl, 2-methylprop-2-yl, 2-methylbut-2cyclopropyl, 1-methylcyclopropyl or cyclohexyl.

3. A compound according to claim 2 selected from the group of compounds consisting of
ethyl RS-2-[2-(2-methylprop-2-yl)pyrimidin-5-yl]-3-methylbutyrate.
ethyl RS-2-[2-(1-methylcyclopropyl)pyrimidin-5-yl]-3-methylbutyrate
ethyl RS-2-(2-prop-2-ylpyrimidin-5-yl)-3-methylbutyrate
ethyl RS-2-[2-(2-methylbut-2-yl)pyrimidin-5-yl]-3-methylbutyrate
ethyl RS-2-(2-cyclopropylpyrimidin-5-yl)-3-methylbutyrate
ethyl RS-2-[4-choro-2-(2-methylprop-2-yl)pyrimidin-5-yl]-3-methylbutyrate
ethyl RS-2-[4-fluoro-2-(2-methylprop-2-yl)pyrimidin-5-yl]-3-methylbutyrate 4. A compound according to claim 1 wherein Q represents a group -OR where R is selected from the group consisting of 3-phenoxybenzyl, 1-cyano-1-(3-phenoxyphenyl)methyl, 2-methyl-3-phenylbenzyl, 4-methyl-2,3,5,6-tetrafluorobenzyl, 4-allyl-2,3,5,6-tetrafluorobenzyl, N-3,4,5,6-tetrahydrophthalimidomethyl, 1-ethynyl-1-(3-phenoxyphenyl)methyl, 5-benzylfur-3-ylmethyl, 6-phenoxypyrid-2-ylmethyl, 1-cyano-1-(6-phenoxypyrid-2-yl)methyl, 1-[1-(6-phenoxypyrid-2-yl)]ethyl, 4-(prop-2-yn-1-yn-1-yl)-2,3,5,6-tetrafluorobenzyl,4-(but-2-yn-1-yl)-2,3,5,6-tetrafluorobenzyl, 4-(3-chloroprop-2-en-1-yl)-2,3,5,6-tetrafluorobenzyl, 2-methoxy-4-methoxymethyl-3,5,6-trifluorobenzyl, 4-methoxymethyl-2,3,5,6-tetrafluorobenzyl, 4-benzyl-2,3,5,6-tetrafluorobenzyl, 3-benzyl-4-fluorobenzyl, 4-(3-trimethylsilylprop-2-yn-1-yl)-2,3,5,6-tetrafluorobenzyl, 4-(2-methylprop-2-en-1-yl)-2,3,5,6-tetrafluorobenzyl, 4-ethoxy-2,3,5,6-tetrafluorobenzyl, 4-trimethylsilyl-2,3,5,6-tetrafluorobenzyl, 4-(but-2-en-1-yl)-2,3,5,6-tetrafluorobenzyl, 4-(2-chloroprop-2-en-1-yl)-2,3,5,6-tetrafluorobenzyl, 4-fluoro-3-phenoxybenzyl, 2-chloro-6-fluorobenzyl, 1-cyano-1-(3-benzyl-4-fluorophenyl)methyl, 3-phenylaminobenzyl, 4-(2,3-dichloroprop-2-en-1-yl)-2,3,5,6-tetrafluorobenzyl, pentafluorobenzyl and 1-cyano-1-(4-fluoro-3-phenoxyphenyl)methyl.

5. A compound according to claim 4 selected from the group of compounds consisting of 4-methyl-2,3,5,6-tetrafluorobenzyl RS-2-[2-(2-methylprop-2-yl)pyrimidin-5-yl]-3-methylbutyrate,
4-allyl-2,3,5,6-tetrafluorobenzyl RS-2-[2-(2-methylprop-2-yl)pyrimidin-5-yl]-3-methylbutyrate,
4-(prop-2-yn-1-yl)-2,3,5,6-tetrafluorobenzyl RS-2-[2-(2-methylprop-2-yl)pyrimidin-5-yl]-3-methylbutyrate,
4-methoxymethyl-2,3,5,6-tetrafluorobenzyl RS-2-[2-(2-methylprop-2-yl)pyrimidin-5-yl]-3-methylbutyrate,
2-methoxy-4-methoxymethyl-3,5,6-trifluorobenzyl RS-2-[2-(2-methylprop-2-yl)pyrimidin-5-yl]-3-methylbutyrate,
4-(prop-2-yn-1-yl)-2,3,5,6-tetrafluorobenzyl RS-2-(2-prop-2-yl-pyrimidin-5-yl)-3-methylbutyrate,
4-(prop-2-yn-1-yl)-2,3,5,6-tetrafluorobenzyl RS-2-[2-(2-methylbut-2-yl)pyrimidin-5-yl]-3-methylbutyrate,
4-(prop-2-yn-1-yl)-2,3,5,6-tetrafluorobenzyl RS-2-(2-cyclopropylpyrimidin-5-yl)-3-methylbutyrate, and
4-(prop-2-yn-1-yl)-2,3,5,6-tetrafluorobenzyl RS-2-[2-(1-methylcyclopropyl)pyrimidin-5-yl]-3-methylbutyrate.

6. An insecticidal and acaricidal composition comprising an insecticidally and acaricidally effective amount of a compound according to claim 1 in association with an insecticidally inert diluent or carrier.

7. A method of combating insect and acarine pests at a locus which comprises treating the locus with an insecticidally and acaricidally effective amount of the composition of claim 6.

* * * * *